(12) United States Patent
Puno

(10) Patent No.: US 9,044,333 B2
(45) Date of Patent: *Jun. 2, 2015

(54) INTER-BODY IMPLANTATION SYSTEM AND METHOD

(75) Inventor: Rolando Puno, Louisville, KY (US)

(73) Assignee: R TREE INNOVATIONS, LLC, Prospect, KY (US)

( * ) Notice: Subject to any disclaimer, the term of this patent is extended or adjusted under 35 U.S.C. 154(b) by 850 days.

This patent is subject to a terminal disclaimer.

(21) Appl. No.: 12/179,614

(22) Filed: Jul. 25, 2008

(65) Prior Publication Data

US 2009/0030423 A1    Jan. 29, 2009

Related U.S. Application Data

(60) Provisional application No. 60/952,434, filed on Jul. 27, 2007.

(51) Int. Cl.
| | | |
|---|---|---|
| *A61F 2/44* | (2006.01) | |
| *A61F 2/46* | (2006.01) | |
| *A61F 2/30* | (2006.01) | |

(52) U.S. Cl.
CPC ........... *A61F 2/442* (2013.01); *A61F 2002/448* (2013.01); *A61F 2/4611* (2013.01); *A61F 2/4684* (2013.01); *A61F 2002/30092* (2013.01); *A61F 2002/30462* (2013.01); *A61F 2002/30507* (2013.01); *A61F 2002/30579* (2013.01); *A61F 2002/30596* (2013.01); *A61F 2002/30785* (2013.01); *A61F 2002/4415* (2013.01); *A61F 2002/4475* (2013.01); *A61F 2002/4627* (2013.01); *A61F 2002/4628* (2013.01); *A61F 2002/4629* (2013.01); *A61F 2210/0014* (2013.01); *A61F 2220/0025* (2013.01); *A61F 2220/0075* (2013.01); *A61F 2002/30121* (2013.01); *A61F 2002/4687* (2013.01)

(58) Field of Classification Search
CPC . A61F 2/442; A61F 2/4611; A61F 2002/448; A61F 2002/4415; A61F 2002/30121; A61F 2220/0025; A61F 2220/0075
USPC ........................................ 606/246; 623/17.11
See application file for complete search history.

(56) References Cited

U.S. PATENT DOCUMENTS

| | | |
|---|---|---|
| 4,481,943 A | 11/1984 | Michelson |
| 4,908,892 A | 3/1990 | Michelson |
| 4,949,435 A | 8/1990 | Michelson |

(Continued)

FOREIGN PATENT DOCUMENTS

| | | | | |
|---|---|---|---|---|
| DE | 19710392 C1 * | 7/1999 | ................ | A61F 2/44 |
| EP | 0637439 | 6/1989 | | |

(Continued)

*Primary Examiner* — David H Willse
*Assistant Examiner* — Javier Blanco

(57) ABSTRACT

A system for implanting an interbody device between adjacent vertebrae comprises an interbody device having a plurality of lobes extending outwardly from a longitudinal rib, and having a relaxed shape approximating the shape of the disc being replaced. An insertion guide is provided having a bore therein from a proximal end to a distal end thereof to accept the interbody device in an unrelaxed shape, wherein the distal end is shaped for insertion into an intervertebral space. The insertion rod may be positioned within the bore of the insertion guide whereby the interbody device is positioned within the intervertebral space by advancing the insertion rod into the insertion guide.

9 Claims, 33 Drawing Sheets

(56) References Cited

U.S. PATENT DOCUMENTS

| | | |
|---|---|---|
| 4,957,495 A | 9/1990 | Kluger |
| 4,959,058 A | 9/1990 | Michelson |
| 4,973,321 A | 11/1990 | Michelson |
| 4,985,019 A | 1/1991 | Michelson |
| 5,009,661 A | 4/1991 | Michelson |
| 5,026,386 A | 6/1991 | Michelson |
| 5,052,373 A | 10/1991 | Michelson |
| 5,059,194 A | 10/1991 | Michelson |
| 5,135,210 A | 8/1992 | Michelson |
| 5,195,526 A | 3/1993 | Michelson |
| 5,250,061 A | 10/1993 | Michelson |
| 5,423,842 A | 6/1995 | Michelson |
| 5,425,772 A | 6/1995 | Brantigan |
| 5,451,227 A | 9/1995 | Michelson |
| 5,531,749 A | 7/1996 | Michelson |
| 5,626,266 A | 5/1997 | Michelson |
| 5,662,300 A | 9/1997 | Michelson |
| 6,032,309 A | 3/2000 | Michelson |
| 6,129,740 A | 10/2000 | Michelson |
| 6,142,997 A | 11/2000 | Michelson |
| D437,055 S | 1/2001 | Michelson |
| 6,175,962 B1 | 1/2001 | Michelson |
| 6,193,721 B1 | 2/2001 | Michelson |
| D440,311 S | 4/2001 | Michelson |
| D442,691 S | 5/2001 | Michelson |
| 6,290,724 B1 | 9/2001 | Marino |
| D449,692 S | 10/2001 | Michelson |
| 6,299,030 B1 | 10/2001 | Michelson |
| D450,122 S | 11/2001 | Michelson |
| 6,332,887 B1 | 12/2001 | Knox |
| 6,338,309 B1 | 1/2002 | Michelson |
| D454,197 S | 3/2002 | Michelson |
| D454,953 S | 3/2002 | Michelson |
| 6,364,880 B1 | 4/2002 | Michelson |
| 6,370,694 B1 | 4/2002 | Michelson |
| D457,242 S | 5/2002 | Michelson |
| 6,383,186 B1 | 5/2002 | Michelson |
| 6,387,130 B1 * | 5/2002 | Stone et al. ............... 623/17.16 |
| D460,188 S | 7/2002 | Michelson |
| D460,189 S | 7/2002 | Michelson |
| D463,560 S | 9/2002 | Michelson |
| 6,575,977 B1 | 6/2003 | Michelson |
| 6,609,322 B1 | 8/2003 | Michelson |
| 6,616,666 B1 | 9/2003 | Michelson |
| 6,620,163 B1 | 9/2003 | Michelson |
| 6,648,891 B2 | 11/2003 | Kim |
| 6,656,178 B1 | 12/2003 | Veldhuizen et al. |
| 6,712,818 B1 | 3/2004 | Michelson |
| 6,740,087 B2 | 5/2004 | Knox |
| 6,767,367 B1 | 7/2004 | Michelson |
| 6,926,718 B1 | 8/2005 | Michelson |
| 6,969,405 B2 | 11/2005 | Suddaby |
| 6,989,031 B2 | 1/2006 | Michelson |
| 7,033,392 B2 | 4/2006 | Schmiel et al. |
| 7,037,339 B2 | 5/2006 | Houfburg |
| 7,063,702 B2 | 6/2006 | Michelson |
| 7,094,239 B1 | 8/2006 | Michelson |
| 7,204,851 B2 | 4/2007 | Trieu et al. |
| 7,264,622 B2 | 9/2007 | Michelson |
| 7,297,147 B2 | 11/2007 | Michelson |
| 8,025,697 B2 * | 9/2011 | McClellan et al. ......... 623/17.11 |
| 2001/0005786 A1 | 6/2001 | Michelson |
| 2001/0016741 A1 | 8/2001 | Burkus et al. |
| 2002/0022843 A1 | 2/2002 | Michelson |
| 2002/0091390 A1 | 7/2002 | Michelson |
| 2002/0128655 A1 | 9/2002 | Michelson |
| 2003/0009223 A1 | 1/2003 | Fehling et al. |
| 2003/0018335 A1 | 1/2003 | Michelson |
| 2003/0023311 A1 | 1/2003 | Trieu |
| 2003/0056795 A1 | 3/2003 | Michelson |
| 2003/0158553 A1 | 8/2003 | Michelson |
| 2003/0181912 A1 | 9/2003 | Michelson |
| 2003/0216740 A1 | 11/2003 | Michelson |
| 2004/0014400 A1 | 1/2004 | Cherian et al. |
| 2004/0035903 A1 | 2/2004 | Michelson |
| 2004/0097930 A1 | 5/2004 | Justis et al. |
| 2004/0117019 A1 * | 6/2004 | Trieu et al. ............... 623/17.11 |
| 2004/0186499 A1 | 9/2004 | Michelson |
| 2004/0220572 A1 | 11/2004 | Michelson |
| 2004/0225361 A1 | 11/2004 | Glenn et al. |
| 2004/0230308 A1 | 11/2004 | Michelson |
| 2004/0230309 A1 | 11/2004 | DiMauro et al. |
| 2004/0249388 A1 | 12/2004 | Michelson |
| 2004/0254736 A1 | 12/2004 | Michelson et al. |
| 2005/0027297 A1 | 2/2005 | Michelson |
| 2005/0027298 A1 | 2/2005 | Michelson |
| 2005/0033433 A1 | 2/2005 | Michelson |
| 2005/0038436 A1 | 2/2005 | Michelson |
| 2005/0038512 A1 | 2/2005 | Michelson |
| 2005/0059971 A1 | 3/2005 | Michelson |
| 2005/0072784 A1 | 4/2005 | Michelson et al. |
| 2005/0171607 A1 | 8/2005 | Michelson |
| 2005/0187544 A1 | 8/2005 | Swanson et al. |
| 2005/0187552 A1 | 8/2005 | Michelson |
| 2005/0216009 A1 | 9/2005 | Michelson |
| 2005/0216010 A1 | 9/2005 | Michelson |
| 2005/0222684 A1 | 10/2005 | Ferree |
| 2005/0267578 A1 | 12/2005 | Michelson |
| 2006/0041259 A1 | 2/2006 | Paul et al. |
| 2006/0085001 A1 | 4/2006 | Michelson |
| 2006/0116769 A1 | 6/2006 | Marnay et al. |
| 2006/0122702 A1 | 6/2006 | Michelson |
| 2006/0142762 A1 | 6/2006 | Michelson |
| 2006/0190083 A1 | 8/2006 | Arnin et al. |
| 2006/0217810 A1 | 9/2006 | Leclercq |
| 2006/0247781 A1 | 11/2006 | Francis |
| 2007/0055274 A1 | 3/2007 | Appenzeller et al. |
| 2007/0067035 A1 | 3/2007 | Falahee |
| 2007/0088436 A1 | 4/2007 | Parsons et al. |
| 2007/0118222 A1 | 5/2007 | Lang |
| 2007/0123986 A1 | 5/2007 | Schaller |
| 2007/0142843 A1 | 6/2007 | Dye |
| 2007/0255413 A1 | 11/2007 | Edie et al. |
| 2007/0276406 A1 | 11/2007 | Mahoney et al. |
| 2008/0058933 A1 | 3/2008 | Garner et al. |
| 2008/0133012 A1 * | 6/2008 | McGuckin ............... 623/17.12 |
| 2008/0177270 A1 | 7/2008 | Sorrenti et al. |
| 2008/0312743 A1 * | 12/2008 | Vila et al. ............... 623/17.16 |
| 2009/0149960 A1 | 6/2009 | Hushka et al. |
| 2009/0177285 A1 | 7/2009 | Frey et al. |
| 2010/0152790 A1 | 6/2010 | Hestad |

FOREIGN PATENT DOCUMENTS

| | | |
|---|---|---|
| EP | 0712607 | 5/1996 |
| EP | 1093760 | 4/2001 |
| EP | 1129668 | 9/2001 |
| EP | 1153574 | 11/2001 |
| EP | 1197181 | 4/2002 |
| EP | 1219248 | 7/2002 |
| EP | 1369357 | 12/2003 |
| EP | 1400221 | 3/2004 |
| EP | 1402836 | 3/2004 |
| EP | 1419741 | 5/2004 |
| EP | 1442732 | 8/2004 |
| EP | 1488755 | 12/2004 |
| EP | 1500372 | 1/2005 |
| EP | 1504735 | 2/2005 |
| EP | 1508307 | 2/2005 |
| EP | 1525853 | 4/2005 |
| EP | 1525863 | 4/2005 |
| EP | 1554995 | 7/2005 |
| EP | 1618848 | 1/2006 |
| EP | 1645248 | 4/2006 |
| EP | 1681021 | 7/2006 |
| EP | 1690508 | 8/2006 |
| EP | 1709920 | 10/2006 |
| EP | 1847229 | 10/2007 |
| WO | 8912431 | 12/1989 |
| WO | 9000037 | 1/1990 |
| WO | 9001298 | 2/1990 |
| WO | 9002524 | 3/1990 |
| WO | 9002574 | 3/1990 |
| WO | 9614799 | 5/1996 |

(56) References Cited

FOREIGN PATENT DOCUMENTS

| | | |
|---|---|---|
| WO | 9627345 | 9/1996 |
| WO | 9640015 | 12/1996 |
| WO | 9640019 | 12/1996 |
| WO | 9640020 | 12/1996 |
| WO | 9834553 | 8/1998 |
| WO | 9834556 | 8/1998 |
| WO | 9963891 | 12/1999 |
| WO | 0042898 | 1/2000 |
| WO | 0025707 | 5/2000 |
| WO | 0028287 | 5/2000 |
| WO | 0066011 | 11/2000 |
| WO | 0066045 | 11/2000 |
| WO | 0106962 | 2/2001 |
| WO | 0156497 | 8/2001 |
| WO | 0156513 | 8/2001 |
| WO | 0180784 | 11/2001 |
| WO | 0195837 | 12/2001 |
| WO | 0203885 | 1/2002 |
| WO | 0217824 | 3/2002 |
| WO | 02058593 | 8/2002 |
| WO | 02062272 | 8/2002 |
| WO | 02069891 | 9/2002 |
| WO | 02076335 | 10/2002 |
| WO | 02078514 | 10/2002 |
| WO | 02098276 | 12/2002 |
| WO | 02098277 | 12/2002 |
| WO | 03020169 | 3/2003 |
| WO | 03065930 | 8/2003 |
| WO | 2004032774 | 4/2004 |
| WO | 2004114195 | 12/2004 |
| WO | 2006044920 | 4/2006 |
| WO | 2006072941 | 7/2006 |
| WO | 2007022194 | 2/2007 |
| WO | 2008016598 | 2/2008 |
| WO | 2008152501 | 12/2008 |

\* cited by examiner

INTER-BODY IMPLANTATION SYSTEM AND METHOD

CROSS-REFERENCE TO RELATED APPLICATIONS

This application claims the benefit of U.S. Provisional Patent Application Ser. No. 60/952,434 filed Jul. 27, 2007 and entitled "Inter-Body Implantation System and Method".

BACKGROUND OF THE INVENTION

1. Field of the Invention

The present invention relates generally to an inter-body device for intervertebral disc replacement or inter-body spinal fusion and more specifically to a system including a device for disc replacement or an inter-body device for spinal fusion and an insertion system and method for placing the devices in an intervertebral space utilizing a plurality of surgical approaches.

2. Description of the Related Art

The normal human spine is comprised of seven cervical, twelve thoracic, and five lumbar vertebrae. Intervertebral discs are interposed between adjacent vertebrae with the exception of the first two cervical vertebrae. The spinal vertebrae are supported by ligaments, tendons and muscles which allow movement such as flexion, extension, lateral bending and rotation.

Motion between vertebrae occurs through the relative motion of the disc and two facet joints. The disc lies in the front or anterior portion of the spine. The facet joints lie laterally on either side of the posterior portion of the spine. The basic shape of a human intervertebral disc is oval, having a depression in a longitudinal side thereof to form a kidney bean shape.

The spine is a flexible structure that is capable of great curvature and twist in a plurality of directions. However, developmental or genetic irregularities, trauma, chronic stress and degeneration due to wear may result in the need for surgical intervention to effect repair. In cases of degeneration (or injury and disease) it may be necessary or desirable to remove a disc that is no longer performing the function of separation between adjacent vertebrae. This is particularly desirable in cases of degeneration or herniation, which often result in chronic and debilitating back pain.

A damaged disc may be replaced with a prosthetic disc that is intended to be functionally identical to the natural disc. Some prior art replacement discs are shaped to approximate the shape of the natural disc that is being replaced, and further are comprised of a flexible material having a shape memory such that the disc may be deformed for insertion through a small area in the spine, then expand to its normal shape once insertion is completed. One of the major difficulties with many prior art discs is that they are most easily inserted utilizing an anterior surgical insertion due to the structure of the spine and arrangement of nerves proximate the spine. The anterior surgical approach to disc replacement is, however, quite invasive.

Furthermore, many prior art disc replacements are complex devices made of a combination of materials and are also bulky and difficult to place properly between adjacent vertebrae. The implantation of these prior art devices requires invasive surgery for proper placement. Additionally, some disc replacements utilize materials such as hydrogels to simulate the gelatinous texture of the natural disc nucleus. However, these materials tend to be easily damaged during implantation and also tend to migrate into undesired areas of the body.

A number of prior art inter-body devices to effect the fusion of adjacent vertebrae to each other are also employed to alleviate the pain and discomfort caused by disc degeneration. Implantation of these prior art devices is typically quite unwieldy and invasive due primarily to their complex structure and the complex geometry of the human spine.

Accordingly, a need exists for an inter-body disc device or a disc replacement device and an implantation system for inserting the interbody fusion or disc replacement device that are robust and surgically minimally invasive for the efficacious replacement of damaged or degenerated intervertebral discs.

BRIEF DESCRIPTION OF THE DRAWING FIGURES

DETAILED DESCRIPTION OF THE PREFERRED EMBODIMENT(S)

Figure 1:
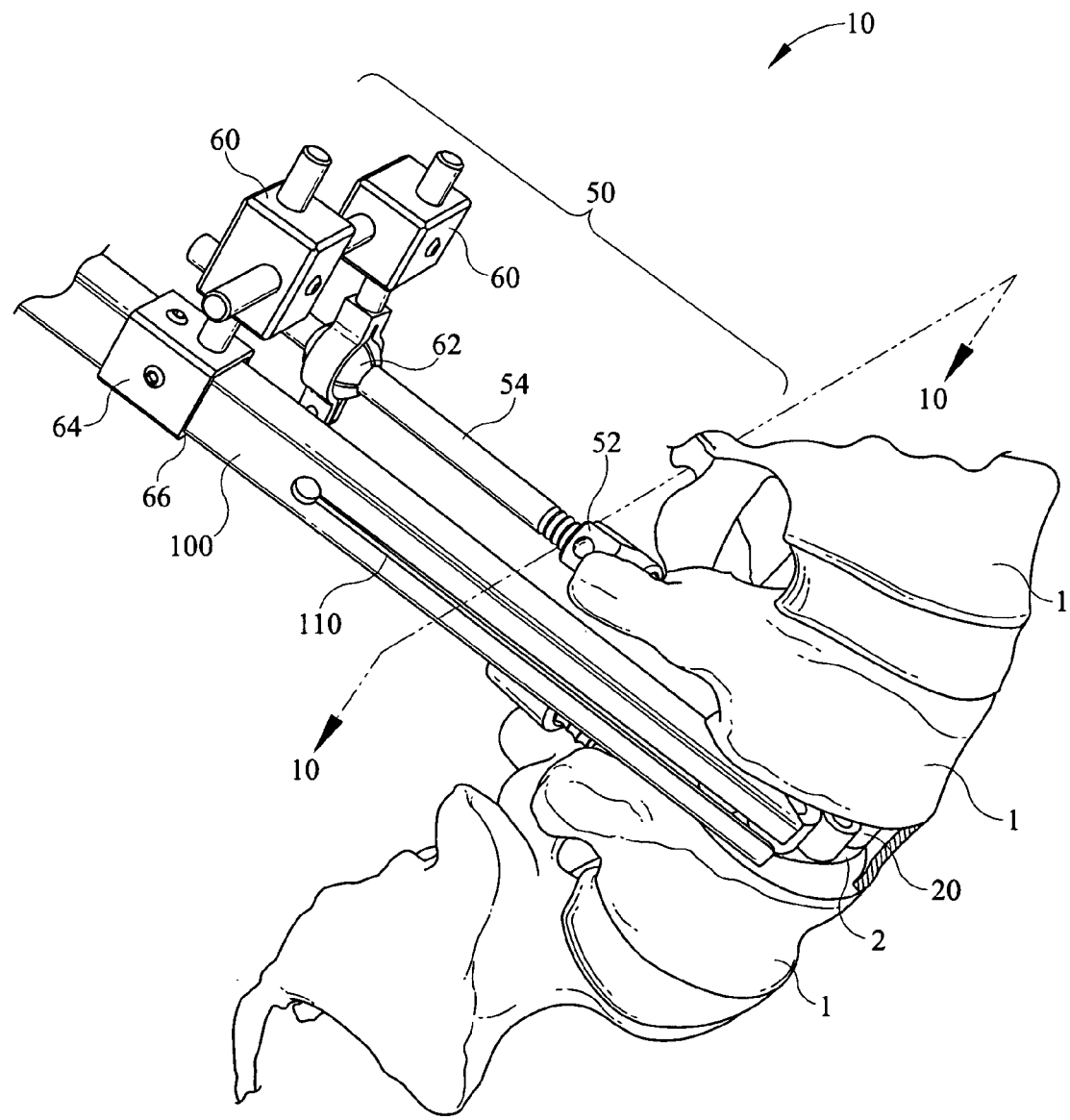
FIG. 1 is a perspective view of a disc replacement system in use in the environment of a human spine in accordance with one embodiment of the present invention.
Figure 2:
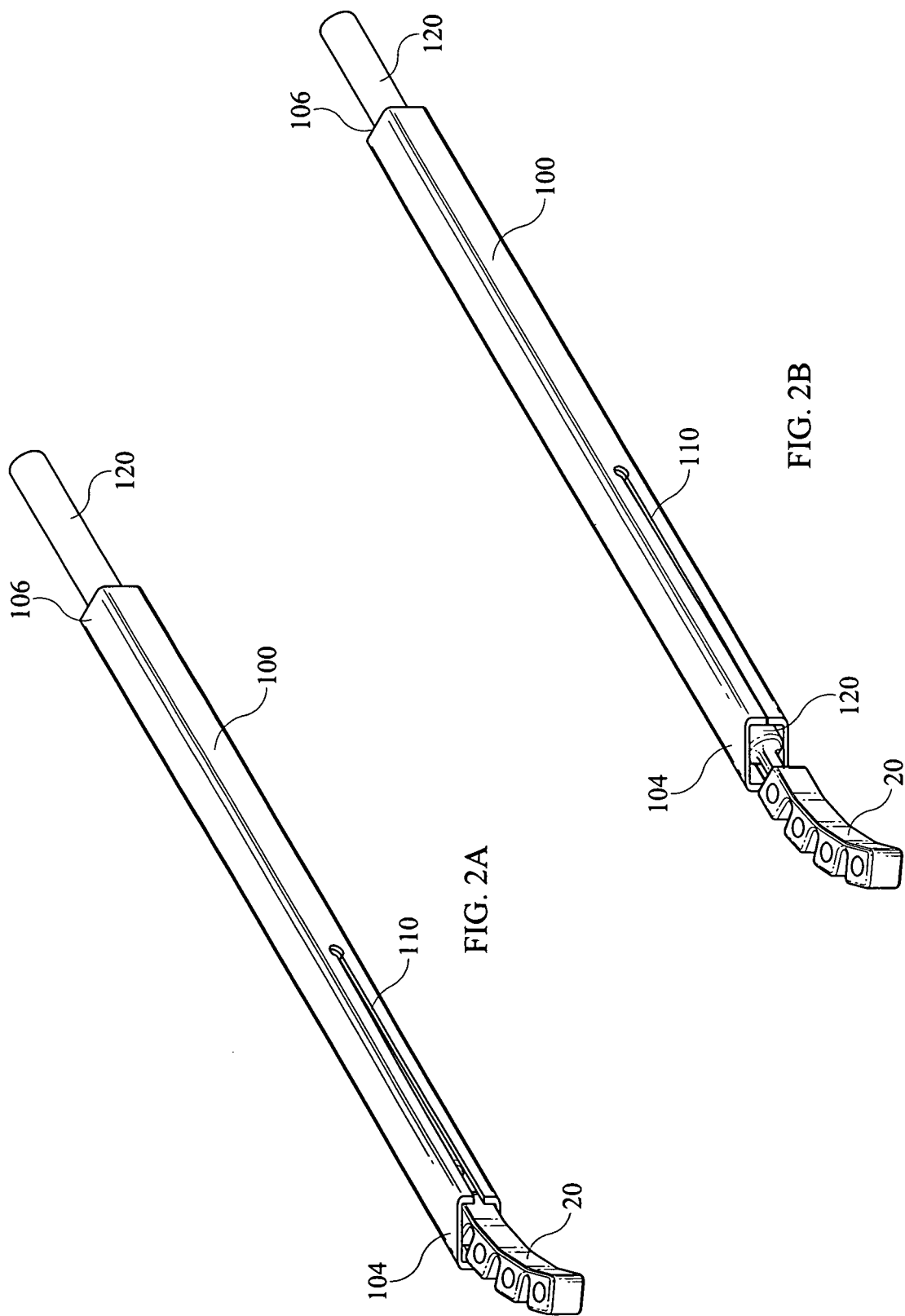
FIG. 2A is a perspective view of an interbody device implantation system in accordance with one embodiment of the present invention.
FIG. 2B is a perspective view of an interbody device implantation system in accordance with one embodiment of the present invention.

Referring now to FIG. 1, and in accordance with a preferred constructed embodiment of the present invention, a system 10 for inserting an inter-body device 20, or an implant 20 for replacement of a disc between adjacent vertebrae 1 comprises a stabilization system 50 and an interbody insertion guide 100 that assists in placing interbody device 20 into an intervertebral space 2. Stabilization system 50 may comprise a conventional pedicle screw 52 that is secured to a vertebra 1 adjacent intervertebral space 2, and a stabilizer rod 54 that may be securely locked to pedicle screw 52 by known fastening means, thereby extending stabilizer rod 54 rigidly outward from vertebra 1.

Furthermore, stabilization system 50 may comprise a pair of spaced, connected links 60, a one of which is secured to stabilizer rod 54 by means of, for example, a collet 62 as shown in FIG. 1. A second link 60 includes a guide 64 that is shaped to slidably accept insertion guide 100 through a bore 66 therein. Insertion guide 100 may thus be carefully positioned through an incision (not shown) and within the intervertebral disc space 2 such that it accurately positions interbody device 20 for insertion as discussed further below. Additionally, stabilization system 50 enables a surgeon to place interbody device 20, or a trial implant as discussed further below, into disc space 2 then take an x-ray or equivalent image to determine if device 20 is properly positioned and further if device 20 is, or is not an appropriate size or shape for the patient's spinal geometry, then remove interbody device 20 or a trial implant, if necessary, without the need for removing insertion guide 100. This feature of the invention minimizes corporal damage to a patient since insertion guide 100 need only be placed in intervertebral space 2 once, while various interbody devices 20 may be tested for their suitability of purpose.

Referring to drawing FIGS. 2A-5B, and in accordance with one embodiment of the invention, system 10 for insertion of interbody device 20 includes an insertion guide 100 that is shaped to receive interbody device 20 into a bore 102 therein when interbody device 20 is straightened, as will be discussed further herein below. Insertion guide 100 may be constructed from plastic, aluminum, polycarbonate, or any other generally rigid material.

Insertion guide 100 further comprises a distal end 104 that is placed in intervertebral space 2, and a proximal end 106. Bore 102 extends entirely through guide 100, from distal end 104 to proximal end 106. A longitudinal compression channel 110, or a plurality thereof, is provided along a portion of insertion guide 100 proximate the distal end 104 thereof. Compression channel 110 enables the distal end 104 of insertion guide 100 to be compressed slightly, and also to expand slightly. This feature of the invention permits ease of insertion of guide 100 distal end 104 into disc space 2 and also effects distraction of the space while interbody device 20 is being inserted, since interbody device 20 may cause compression channel 110 to expand outwardly somewhat as it is advanced through bore 102 into distal end 104. The insertion guide 100 additionally aids in protection of the nerves proximate vertebrae 1 while interbody device 20 is being inserted between adjacent vertebrae 1. A plurality of compression channels 110 may be provided in insertion guide 100 distal end 104 to provide for a more even compression of guide 100 as it enters disc space 2. In the embodiments of the invention depicted in FIGS. 2A, 2B, 4A and 4B, the insertion guide 100 has a longitudinal axis that is essentially straight. This feature of the insertion guide 100 permits a posterior surgical approach to interbody device 20 insertion that is minimally invasive and thus advantageous over many known anterior surgical disc replacement and interbody fusion techniques.

Figure 4A:
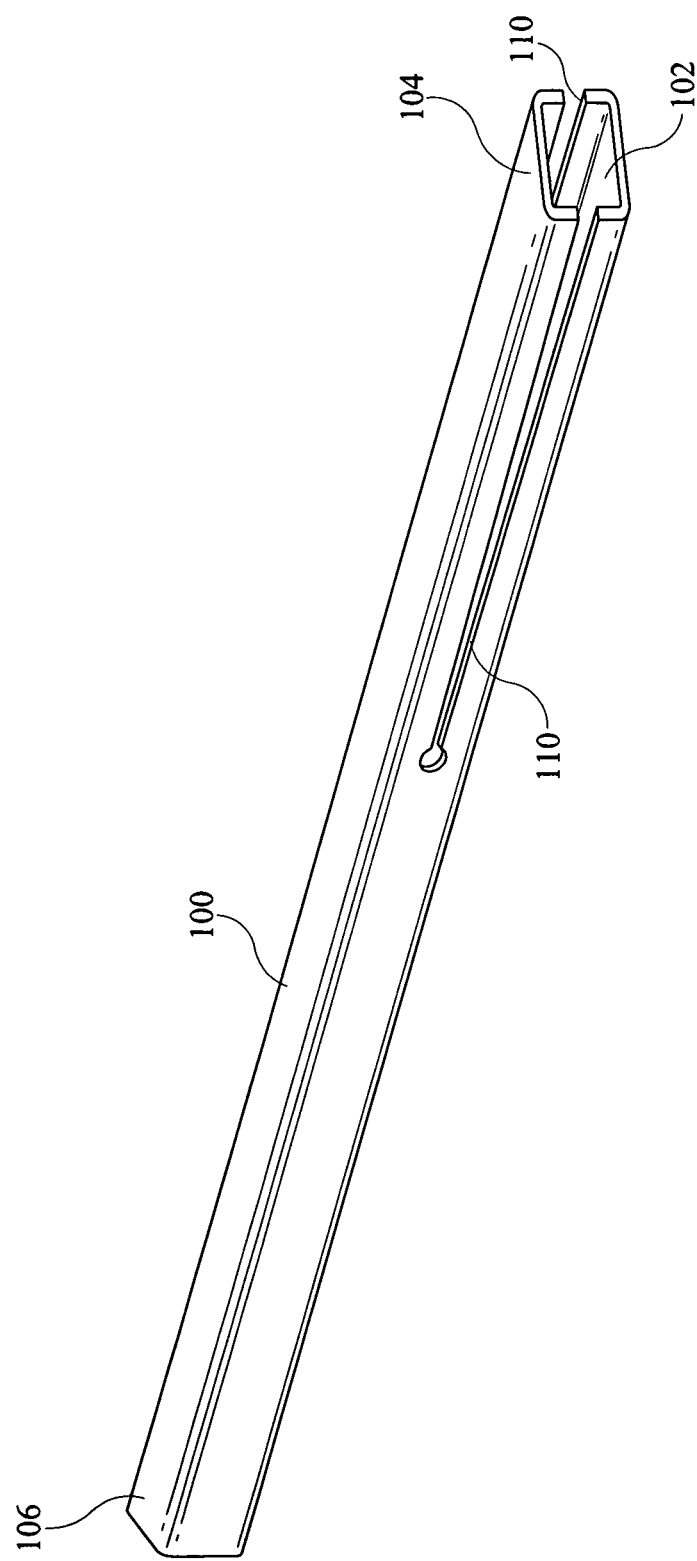
FIG. 4A is a perspective view of an interbody device insertion guide in accordance with one embodiment of the present invention.
Figure 4B:
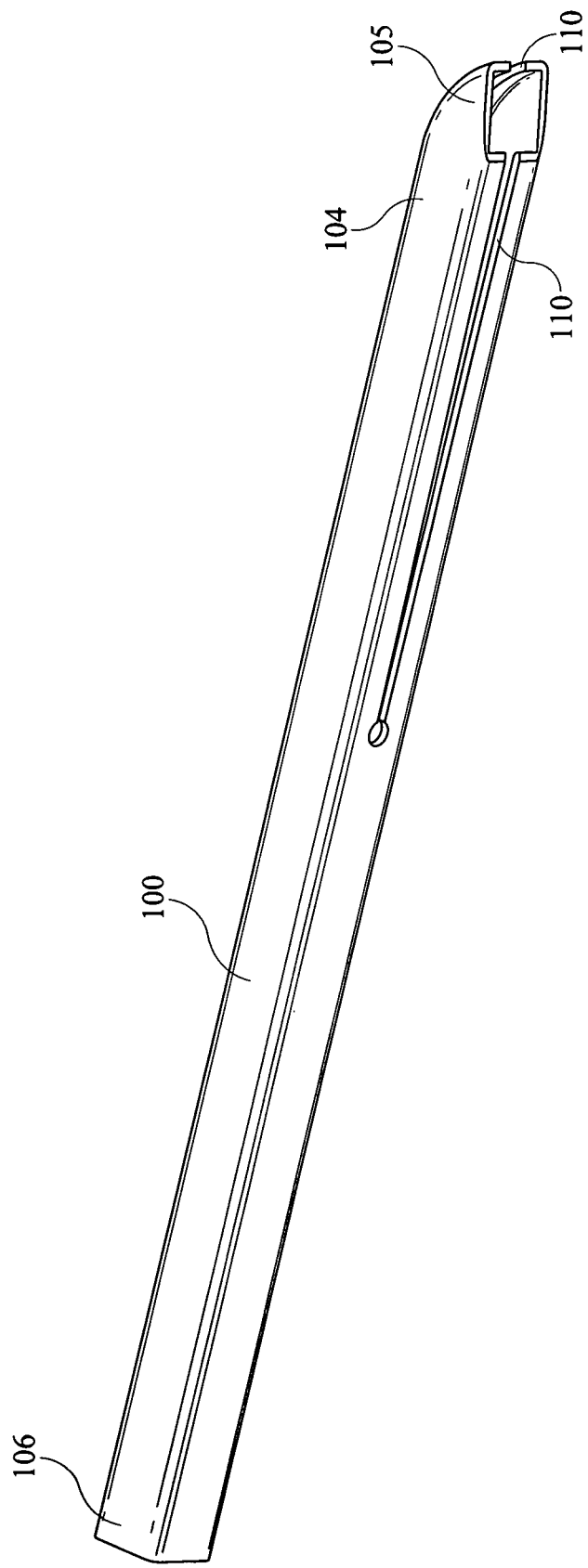
FIG. 4B is a perspective view of an interbody device insertion guide in accordance with one embodiment of the present invention.
Figure 5A:
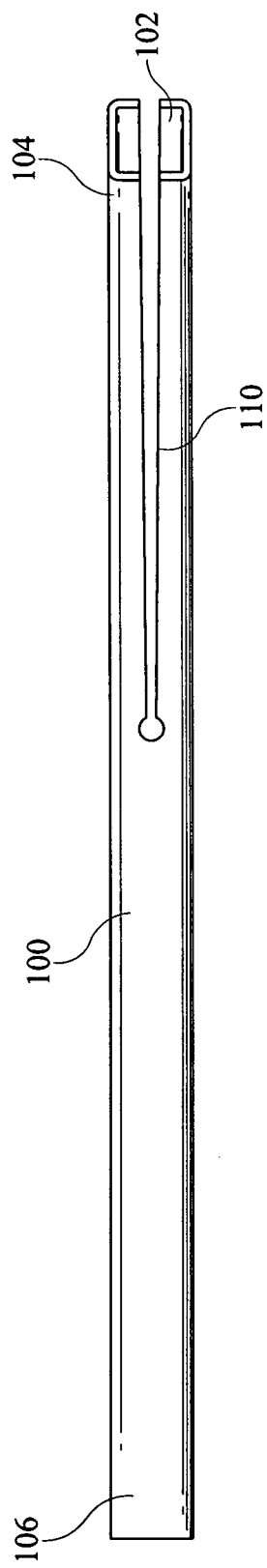
FIG. 5A is an elevation view of an interbody device insertion guide in accordance with one embodiment of the present invention.
Figure 5B:
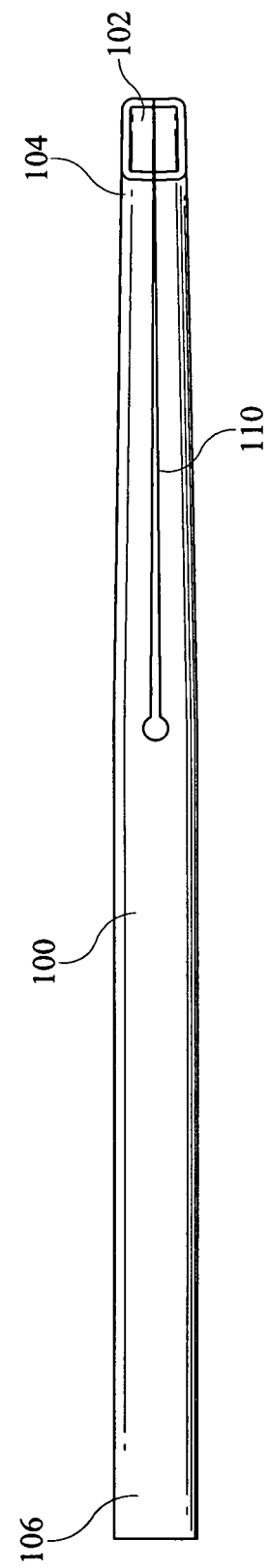
FIG. 5B is an elevation view of an interbody device insertion guide in accordance with one embodiment of the present invention.
Figure 11A:
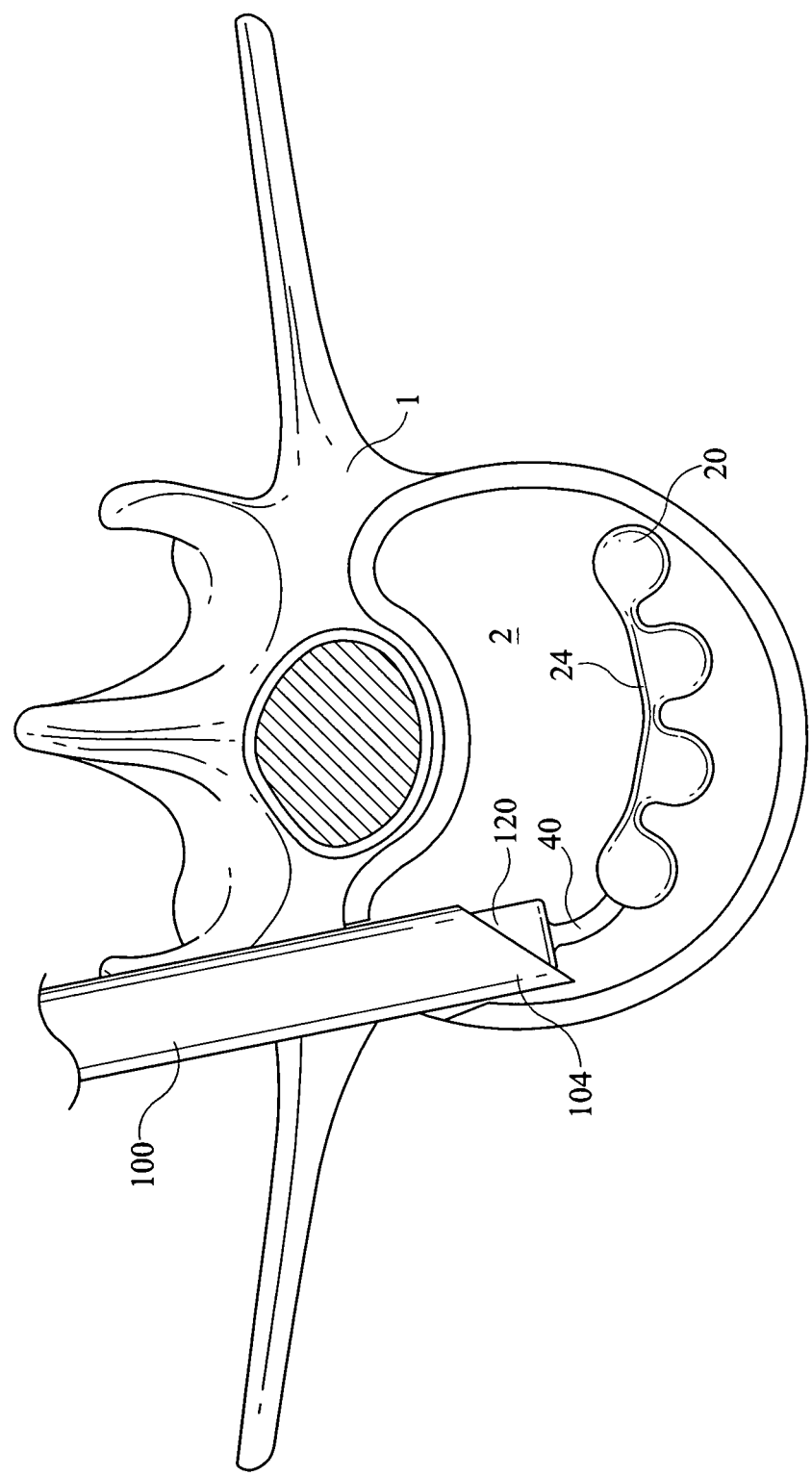
FIG. 11A is a cross-sectional view of an interbody device being inserted into an intervertebral space in accordance with one embodiment of the invention.
Figure 11B:
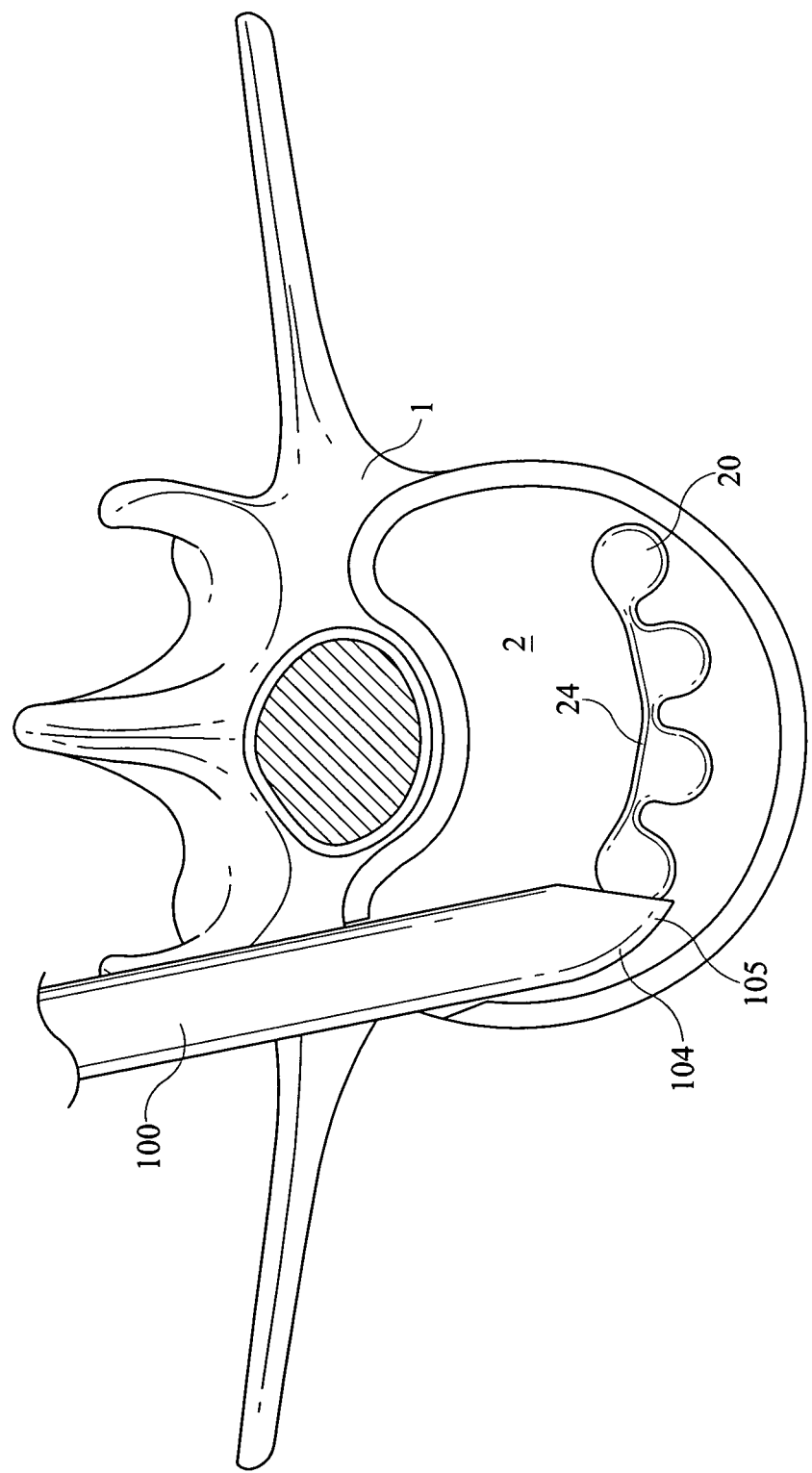
FIG. 11B is a cross-sectional view of an interbody device being inserted into an intervertebral space in accordance with one embodiment of the invention.

As best seen in FIG. 4B, distal end 104 of insertion guide 100 may include a curved or arcuate tip 105 that directs proper placement of interbody device 20 by turning device 20 as it exits distal end of guide 100. An exemplary insertion of interbody device 20 utilizing an insertion guide 100 having arcuate tip 105 is depicted in FIG. 11B, and will be discussed in further detail herein below. It should be noted that the degree of curvature of arcuate tip 105 and the angle at which interbody device 20 exits distal end 104 may be modified as required by a given application without departing from the scope of the present invention.

Figure 3:
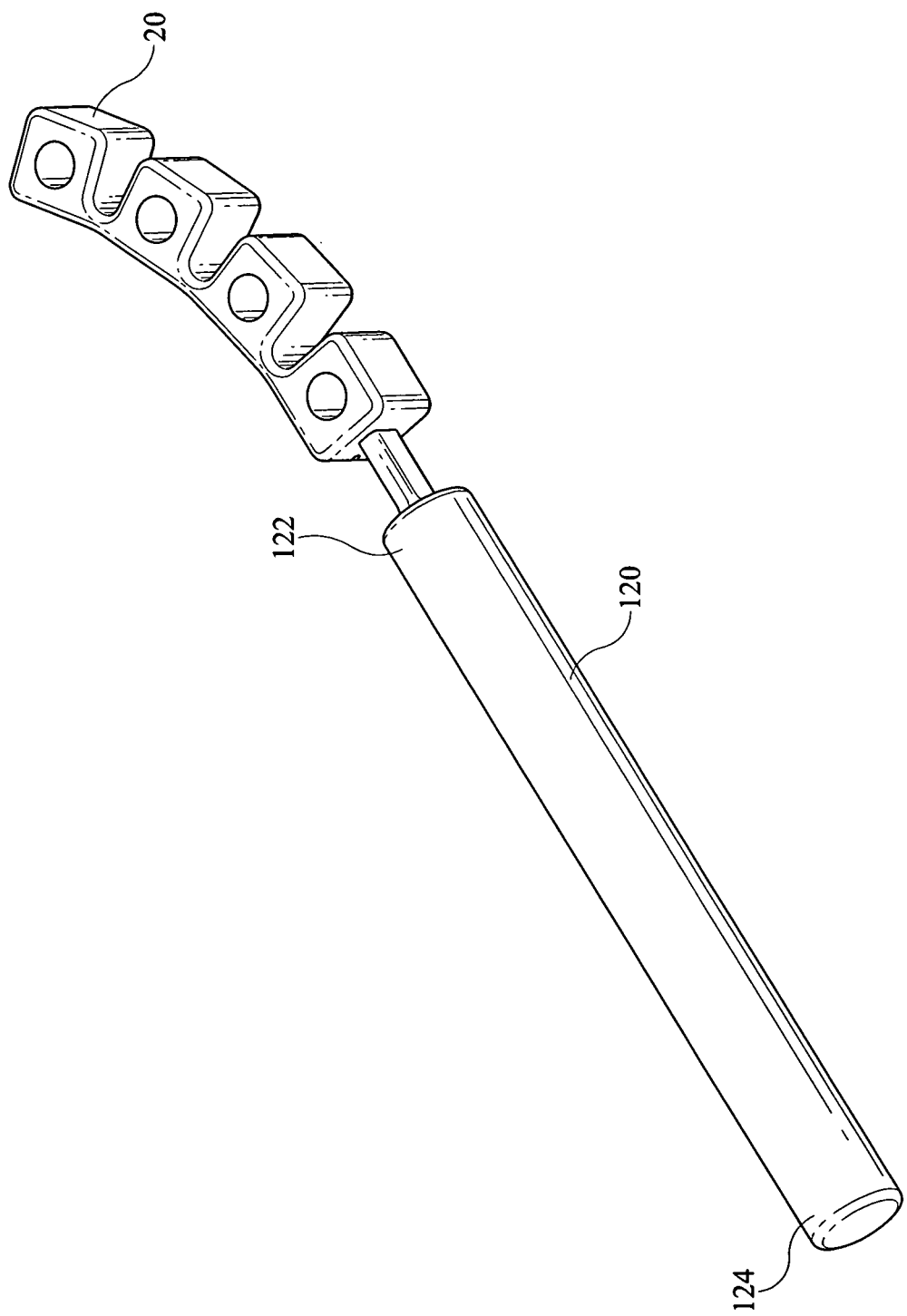
FIG. 3 is a perspective view of an insertion rod secured to an interbody device in accordance with one embodiment of the present invention.

Referring to FIGS. 2A, 2B and 3, an insertion rod 120 is provided that is slidably received into bore 102 of insertion guide 100 through proximal end 106 thereof. Insertion rod 120 has a distal end 122 that may be secured to interbody device 20 and a proximal end 124 that is pushed through bore 102 of insertion guide 100 to advance interbody device 20 into intervertebral space 2.

Figure 12A:
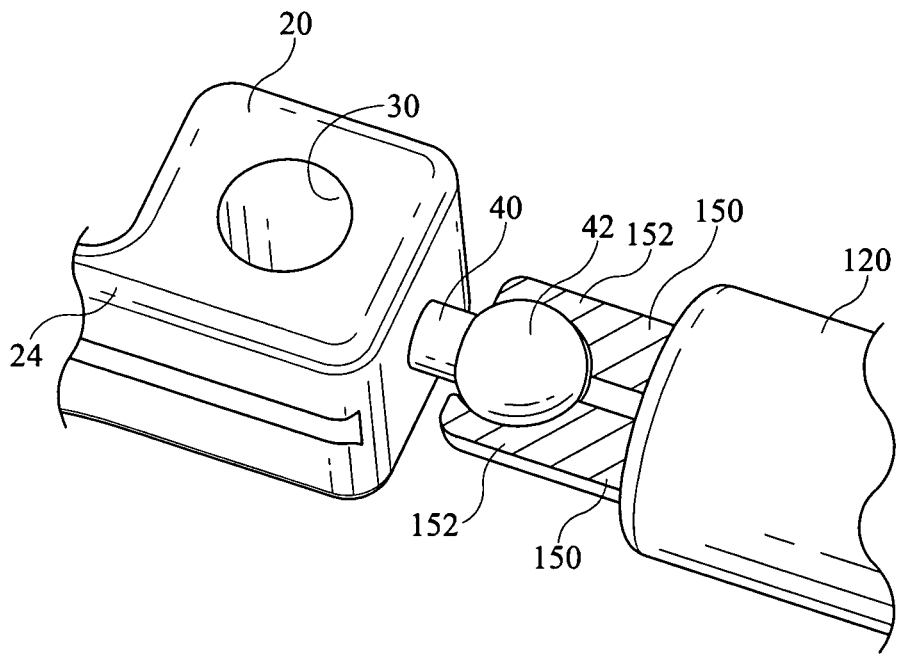
FIG. 12A is a perspective view of an insertion rod secured to an interbody device in accordance with one embodiment of the invention.
Figure 12B:
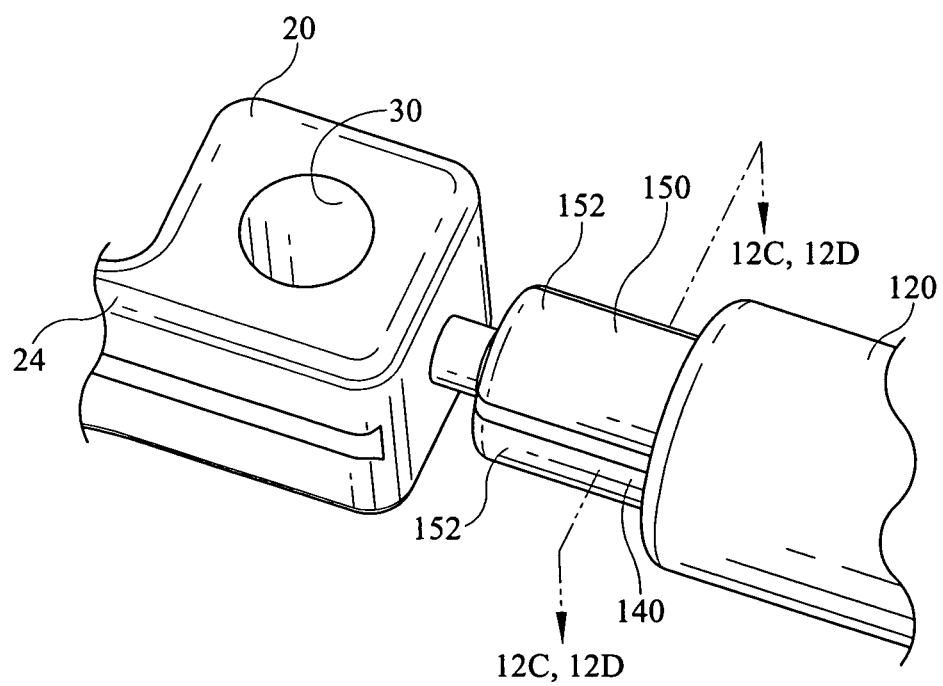
FIG. 12B is a perspective view of an insertion rod secured to an interbody device in accordance with one embodiment of the invention.
Figure 12C:
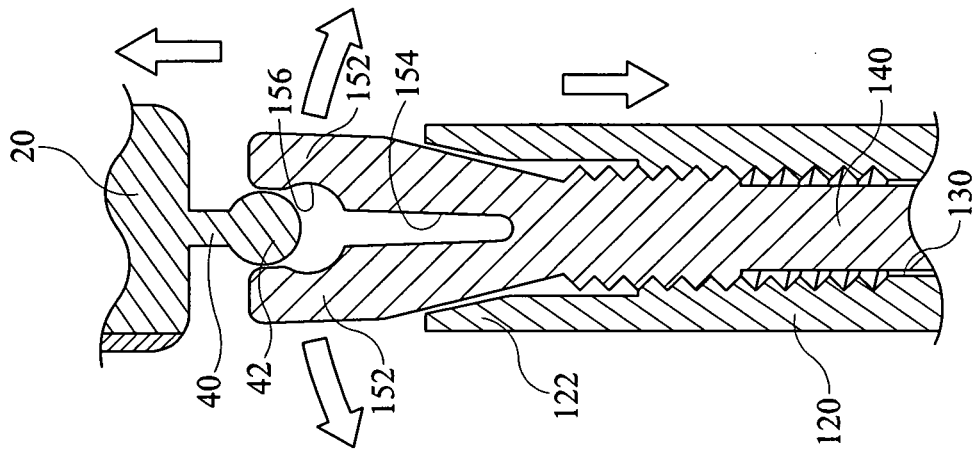
FIG. 12C is a cross sectional view of an insertion rod secured to an interbody device taken along the line 12C-12C of FIG. 12B in accordance with one embodiment of the invention.
Figure 12D:
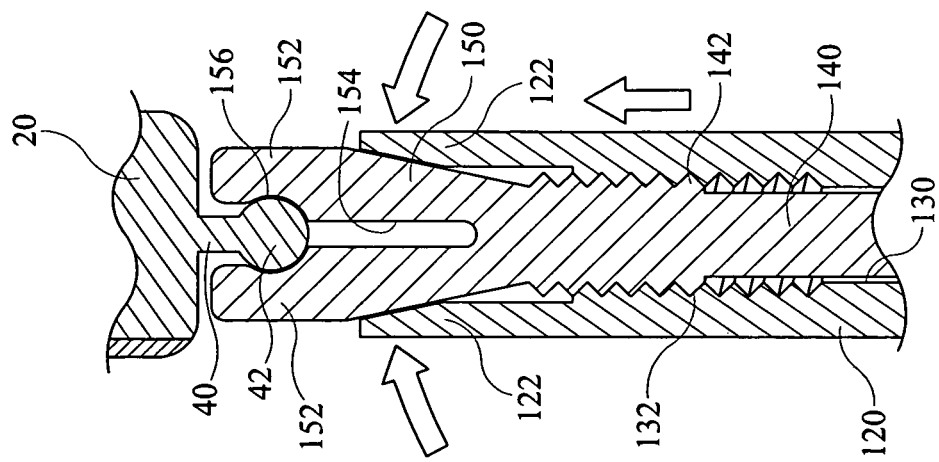
FIG. 12D is a cross-sectional view of an insertion rod releasing an interbody device in accordance with one embodiment of the invention.

Referring now to FIGS. 12A-12D, in an exemplary embodiment of the invention 10, insertion rod 120 may comprise a central bore 130 having a plurality of helical threads 132 disposed therein proximate the distal end 122 of rod 120, and further include an interior rod 140 disposed in central bore 130 that includes a plurality of mating threads 142 for engaging threads 132 of insertion rod 120 such that insertion rod 120 and interior rod 140 are threadably engaged. Interior rod 140 includes a distal clamping end 150 terminating in a plurality of fingers 152 separated by a slot 154. Additionally, each finger 152 includes an engagement surface 156 at an interior portion thereof for engaging a complementary surface provided on interbody device 20. As can be seen in FIGS. 12C and 12D, as interior rod 140 is rotated and thus advanced from distal end 122 of insertion rod 120, fingers 152 expand outwardly thereby releasing engagement surface 156 from contact with interbody device 20. Accordingly, insertion rod 120 may be used by a surgeon to readily insert interbody device 20 into intervertebral space 2 by advancing insertion rod 120 through guide 100, then simply rotating interior rod 140 to release interbody device 20 therefrom. As long as fingers 152 remain inside distal end 122 of insertion rod 120, interbody device 20 is held securely.

Interior rod 140 may be comprised of a flexible memory metal material to enable fingers 152 to expand outwardly and be compressed inwardly. As best seen in FIG. 12C, slot 154 permits fingers 152 to be pushed together or compressed while they are disposed inside distal end 122 of insertion rod 120. As best seen in FIG. 12D, fingers 152 expand outwardly to a relaxed position, thus releasing interbody device 20 once clamp end 150 exits distal end 122 of insertion rod 120. In this fashion, interior rod 140 may be releasably secured to a variety of interbody devices 20 until the devices 20 are properly positioned, as will be discussed in greater detail herein below.

Figure 6A:
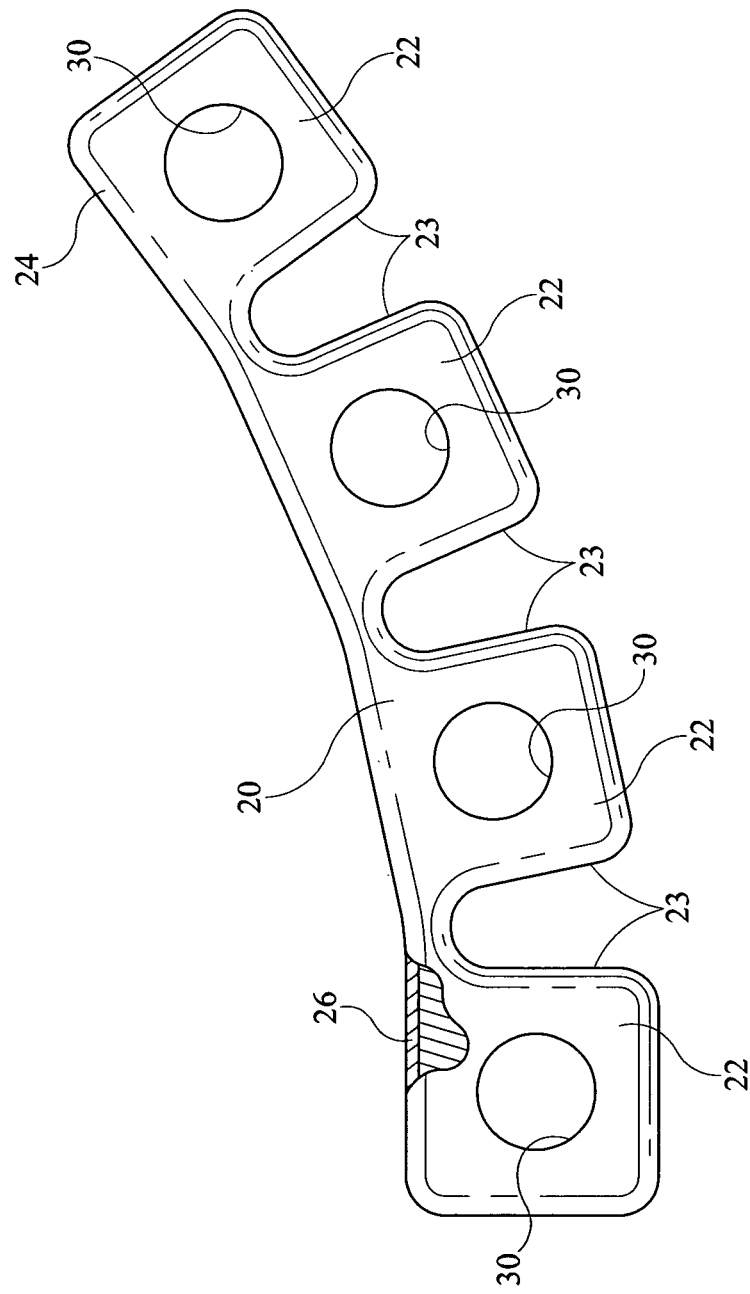
FIG. 6A is a plan view of an interbody device in accordance with one embodiment of the present invention.
Figure 6B:
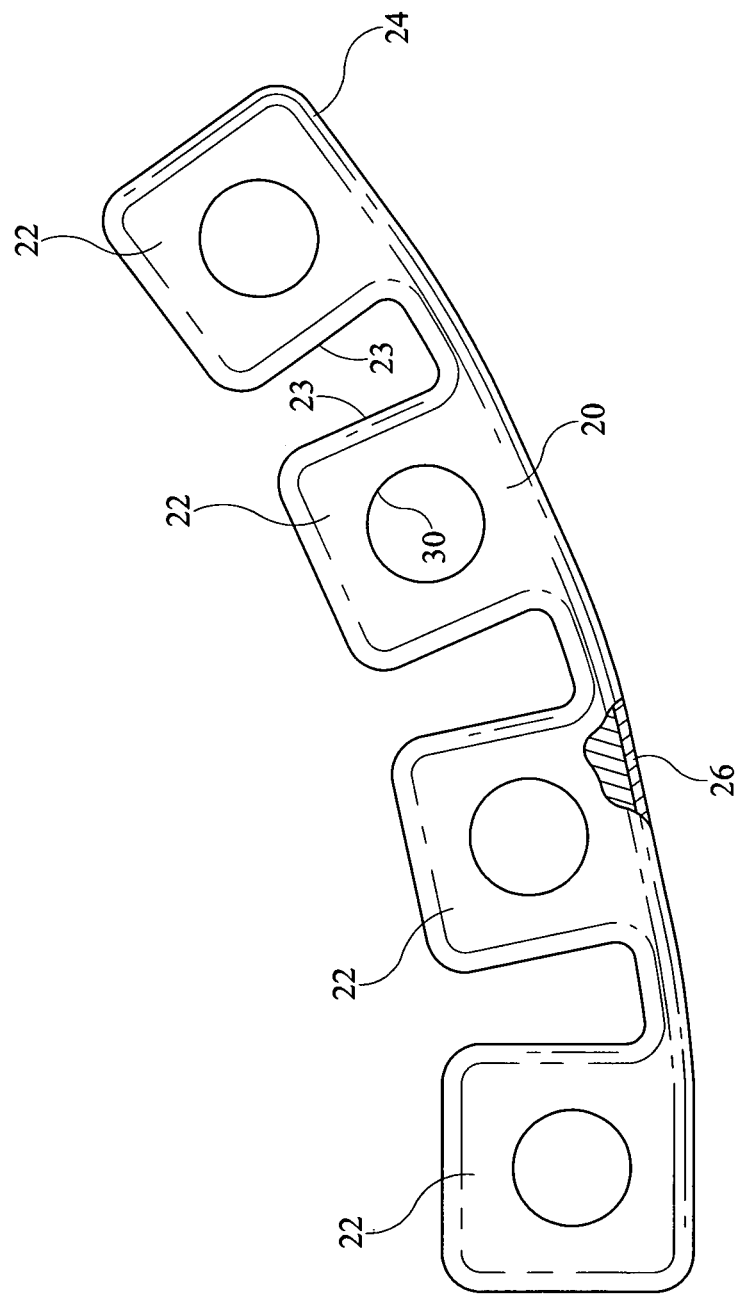
FIG. 6B is a plan view of an interbody device in accordance with one embodiment of the present invention.
Figure 7A:
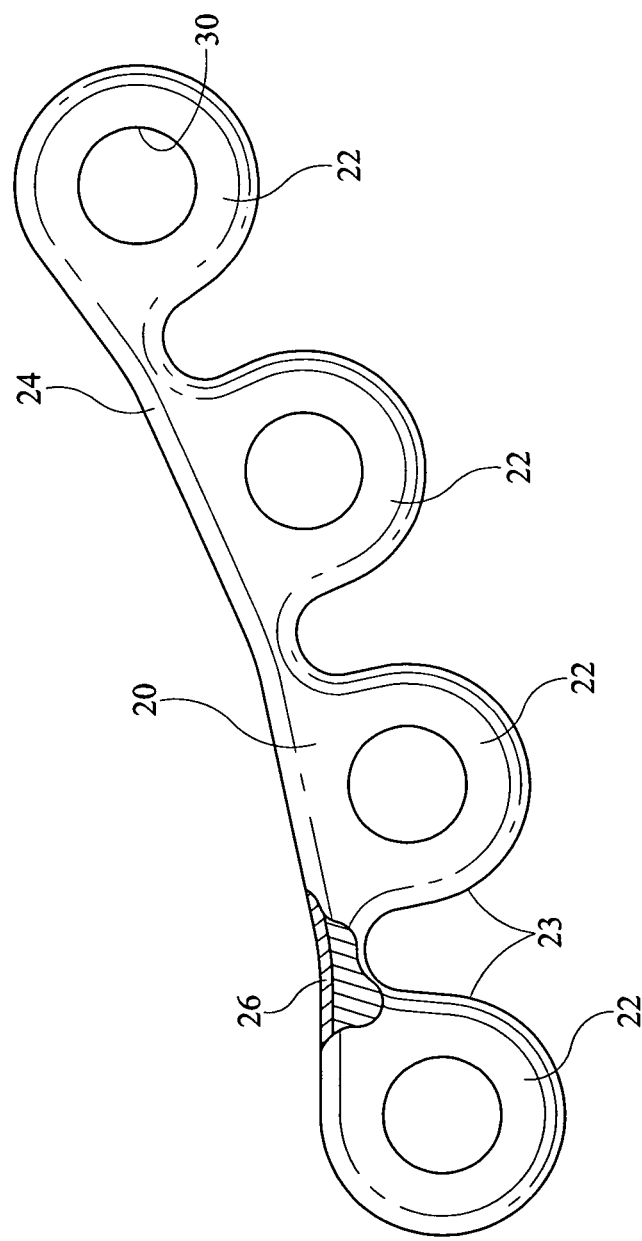
FIG. 7A is a plan view of an interbody device in accordance with one embodiment of the present invention.
Figure 7B:
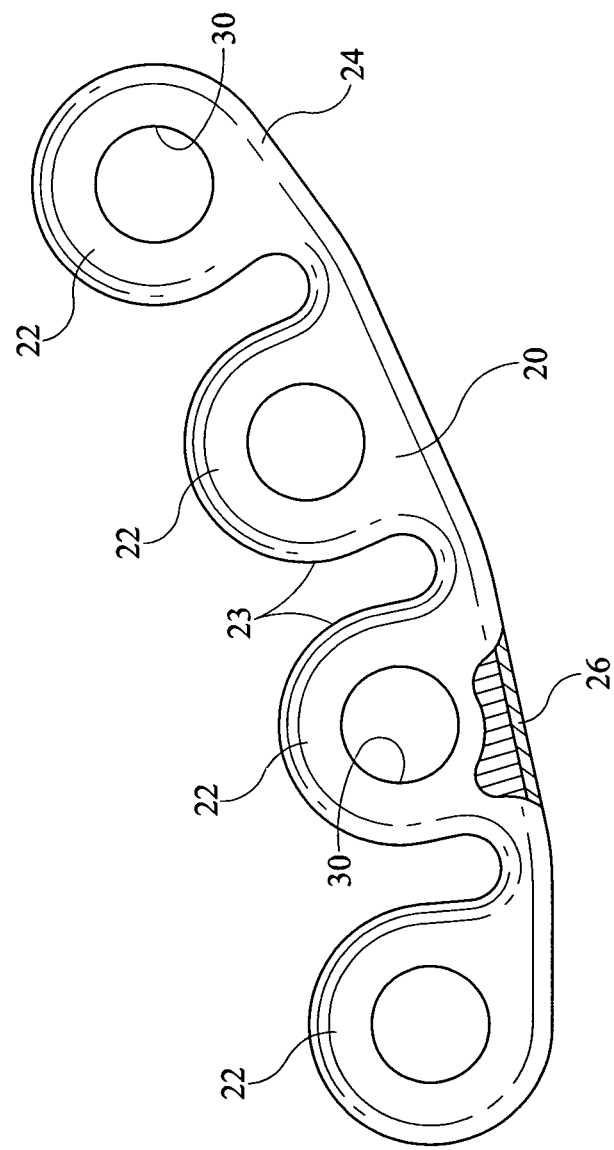
FIG. 7B is a plan view of an interbody device in accordance with one embodiment of the present invention.
Figure 8A:
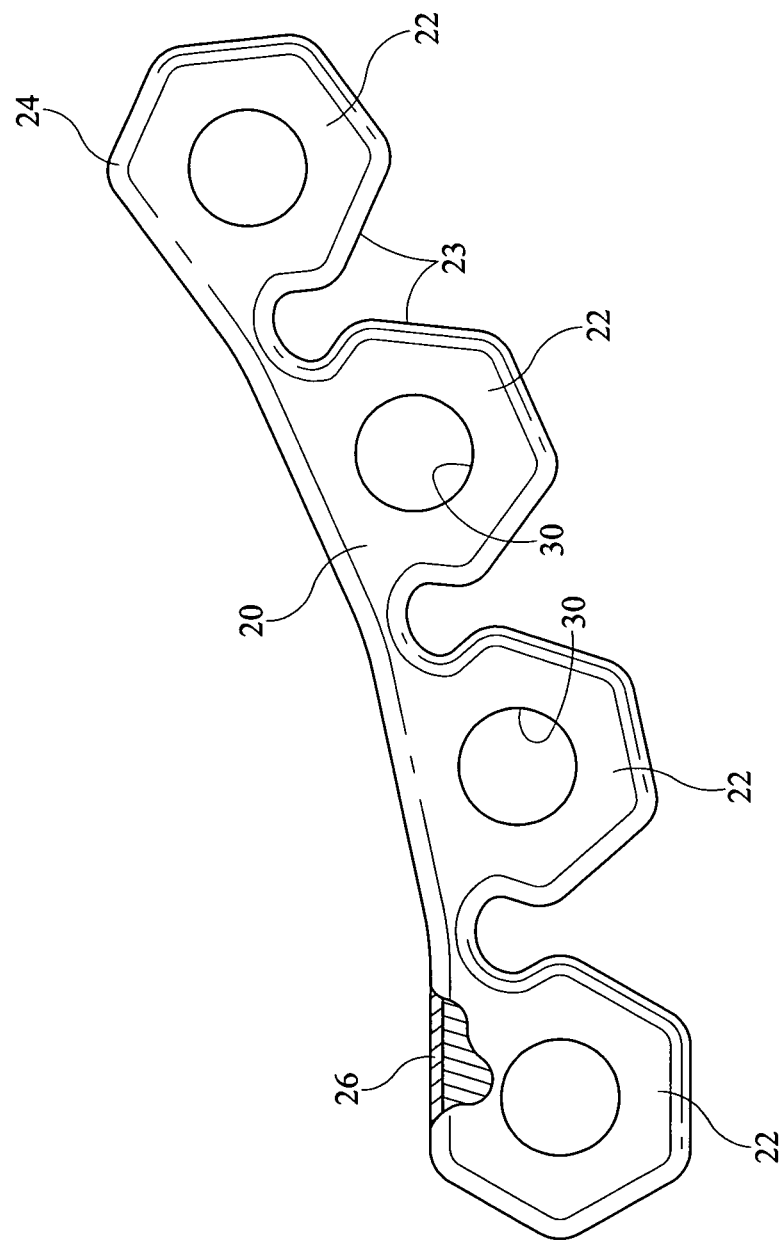
FIG. 8A is a plan view of an interbody device in accordance with one embodiment of the present invention.
Figure 8B:
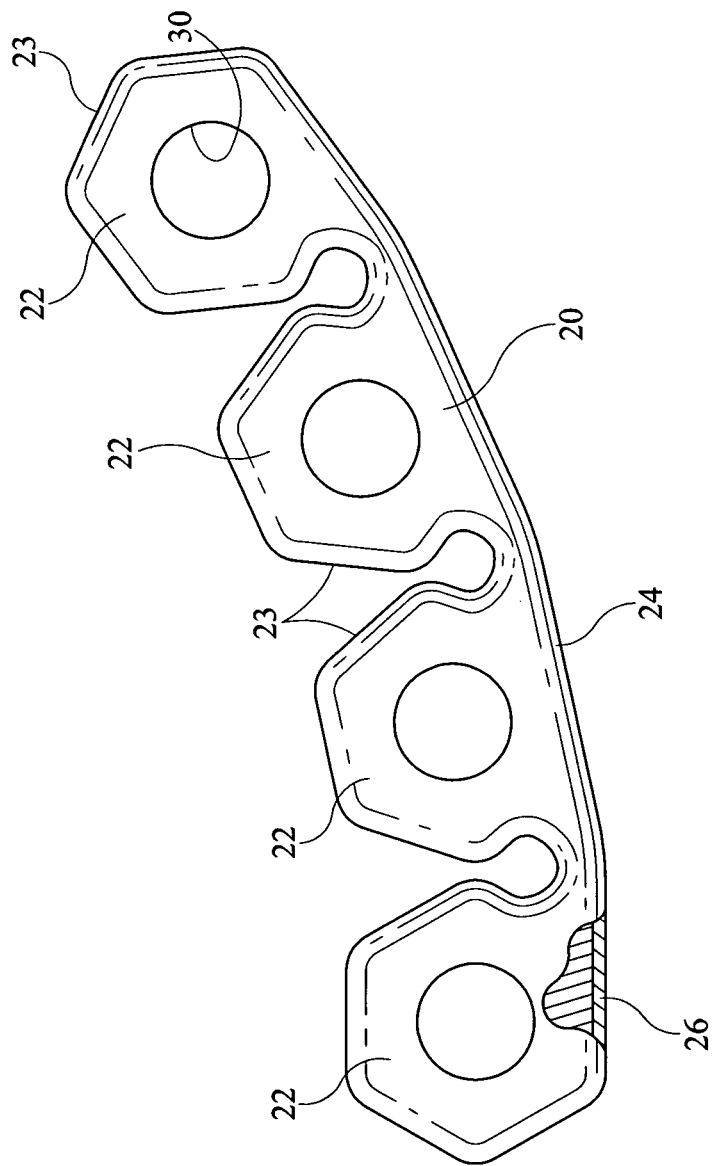
FIG. 8B is a plan view of an interbody device in accordance with one embodiment of the present invention.

Referring now to FIGS. 6A and 6B, interbody device 20 may comprise a plurality of lobes 22 extending from a longitudinal axis 24 that extends substantially along the length of interbody device 20. Each lobe 22 terminates in a side or sides 23, and is connected to and integral with axis 24. It should be noted that throughout the detailed description reference will be made to an interbody device 20 to be inserted between adjacent spinal vertebrae 1 to effect the fusion thereof. However, interbody device 20 referred to herein can also be an implant to effect disc replacement without departing from the scope of the present invention.

Interbody device 20 is preferably formed of a material that is durable and non-reactive. A wide variety of biocompatible materials may be utilized to manufacture the interbody device 20 of the present invention, including but not limited to biocompatible polymers, elastomeric materials, hydrogels, hydrophilic polymers, shape memory polymers, and shape memory metals. It is understood that one of ordinary skill in the art would be aware of a variety of materials suitable for such implantation. In one embodiment of the invention, interbody device 20 is comprised of a carbon fiber material while in another, interbody device 20 is comprised of a polyetheretherketone (PEEK) material.

Interbody device 20 may further comprise a longitudinal elastic rib 26, disposed inside longitudinal axis 24 to assist interbody device 20 in retaining its shape when in a relaxed state. Elastic rib 26 may be comprised of, for example, a memory metal. Furthermore, in one embodiment of the invention the entire interbody device 20 may be comprised of a memory material, such as a memory metal, which obviates the need for elastic rib 26. As seen in FIGS. 6A and 6B the interbody device 20 is formed in such a manner that in its "relaxed" state it generally approximates the shape of the disc that it is intended to replace, depending upon which vertebrae 1 it is intended to separate. In any other shape, interbody device 20 is "unrelaxed". The elastic properties of interbody device 20, as well as the shape memory of rib 26, provides interbody device 20 with a requisite shape memory that permits it to be straightened for insertion between vertebrae 1, yet assume a disc-like shape once insertion is complete, as will be discussed further herein below. Interbody devices 20 may be shaped and sized as required to substantially fill and conform to the cavity or intervertebral space 2 between adjacent vertebrae 1 as necessary for a specific patient. As one example, the height of lobes 22 may be varied to accommodate the lordotic angle of disc space 2.

Figure 9:
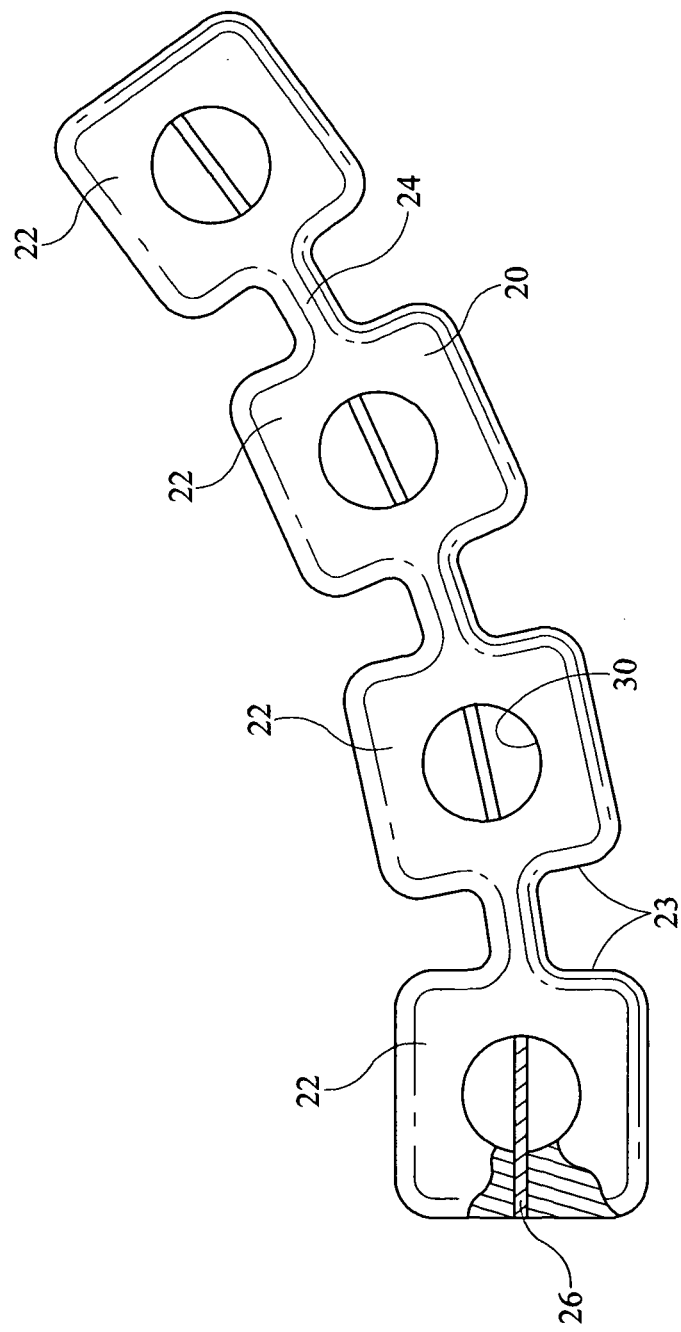
FIG. 9 is a plan view of an interbody device in accordance with one embodiment of the present invention.

Additionally, as shown in FIGS. 6A and 6B, lobes 22 of interbody device 20 may be disposed on either side of longitudinal axis 24, to accommodate variable spinal geometries. Furthermore, the shapes of lobes 22 may also be varied. Exemplary lobe 22 shapes are depicted in FIGS. 6A-8B, wherein lobes 22 may be substantially square with chamfered edges, generally circular, or semi-hexagonal in shape. Additionally, in another embodiment of the present invention as depicted in FIG. 9, rib 26 may be routed through a central longitudinal axis 24 of interbody device 20, which connects a plurality of lobes 22 each to another.

Figure 16A:
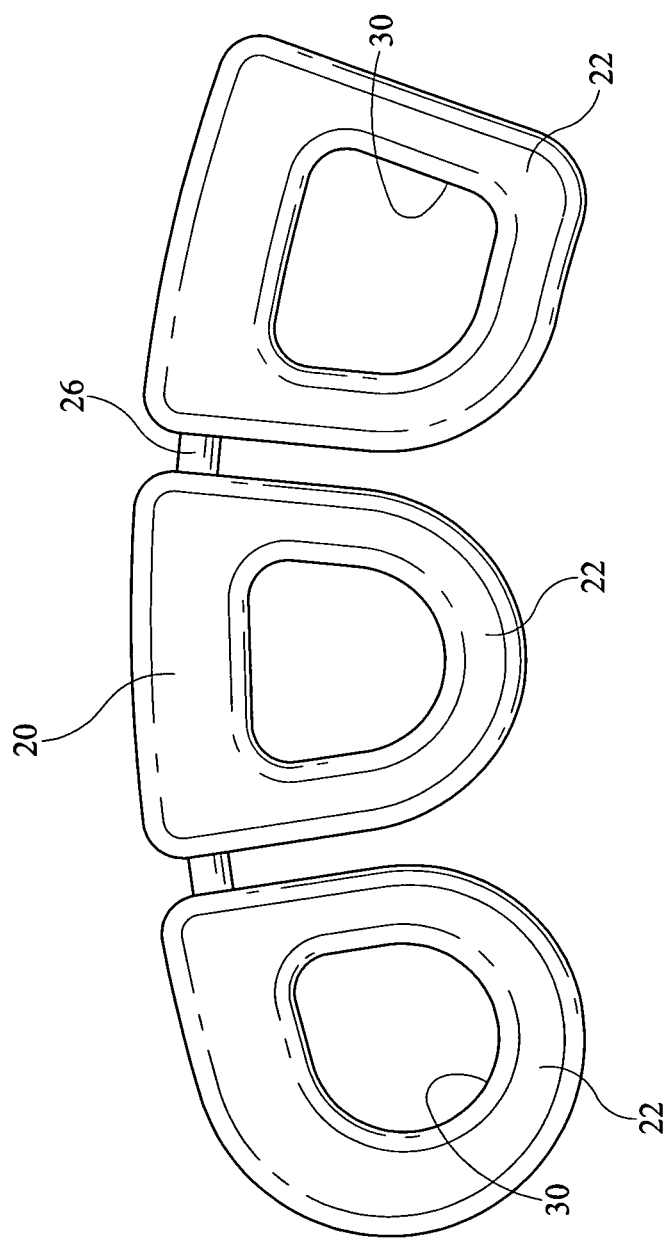
FIG. 16A is a side view of an interbody device in accordance with one embodiment of the invention.
Figure 16B:
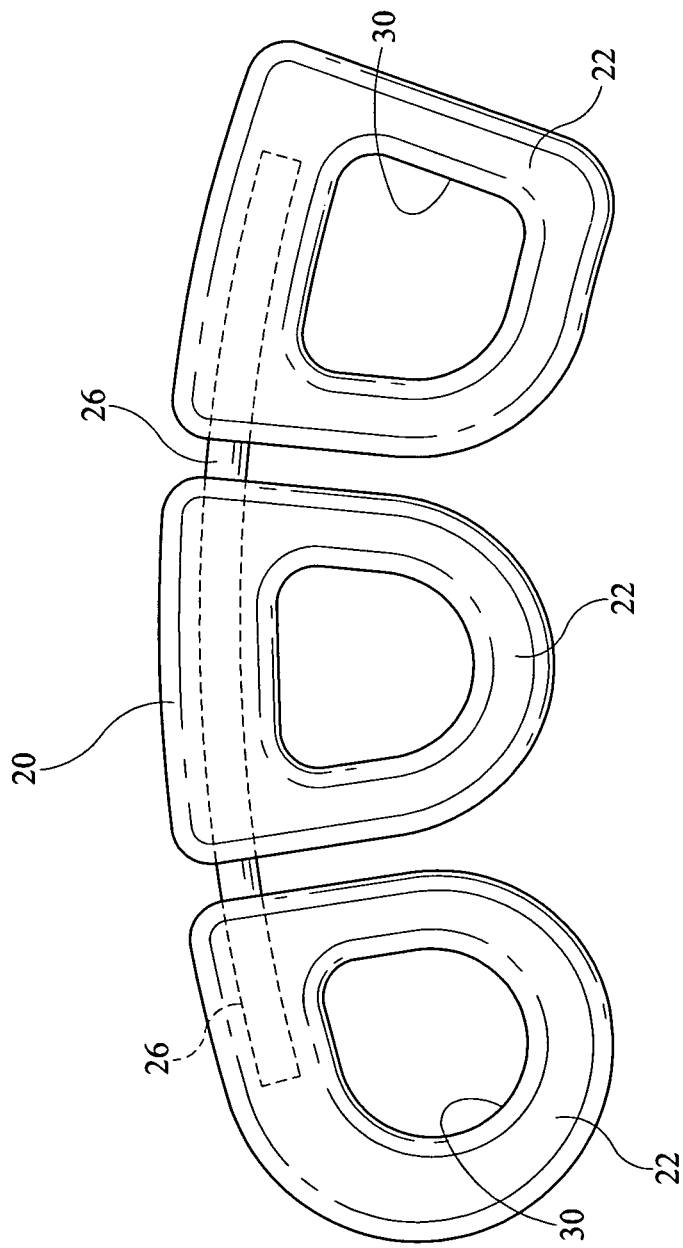
FIG. 16B is a side view, partially in cross-section, of an interbody device showing the placement of a flexible rib therein in accordance with one embodiment of the invention.

FIG. 16A depicts a yet further embodiment of an interbody device 20 in accordance with the present invention wherein rib 26 connects a plurality of lobes 22 without the necessity of a longitudinal section 24 therebetween. In this embodiment of the invention, flexibility of lobes 20 is maximized, since there is no PEEK material interposed between adjacent lobes 20. FIG. 16B depicts the placement of rib 26 within interbody device 20 lobes 22. In one embodiment of the invention, the material comprising lobes 22 is bonded to rib 26 such that lobes 22 are secured thereto but are free to flex relative to one another.

Interbody device 20 may further comprise an aperture 30, or simply a depression in each lobe 22 along longitudinal section 24 that permits the sides 23 of lobes 22 to compress or deform slightly under load, thereby enhancing either stability or flexibility of the spine as required, as well as its ability to bear load and absorb impact. Additionally, in applications where interbody device 20 is to be used as an inter-body device aperture 30 can accept a bone graft material or a bone graft substitute material to aid in spinal fusion if required. Additionally, each lobe 22 may be spaced from an adjacent lobe 22 along rib 24 to enable further flexion of interbody device 20 thereby enabling interbody device 20 to straighten without undue deformation of lobes 22.

Figure 16C:
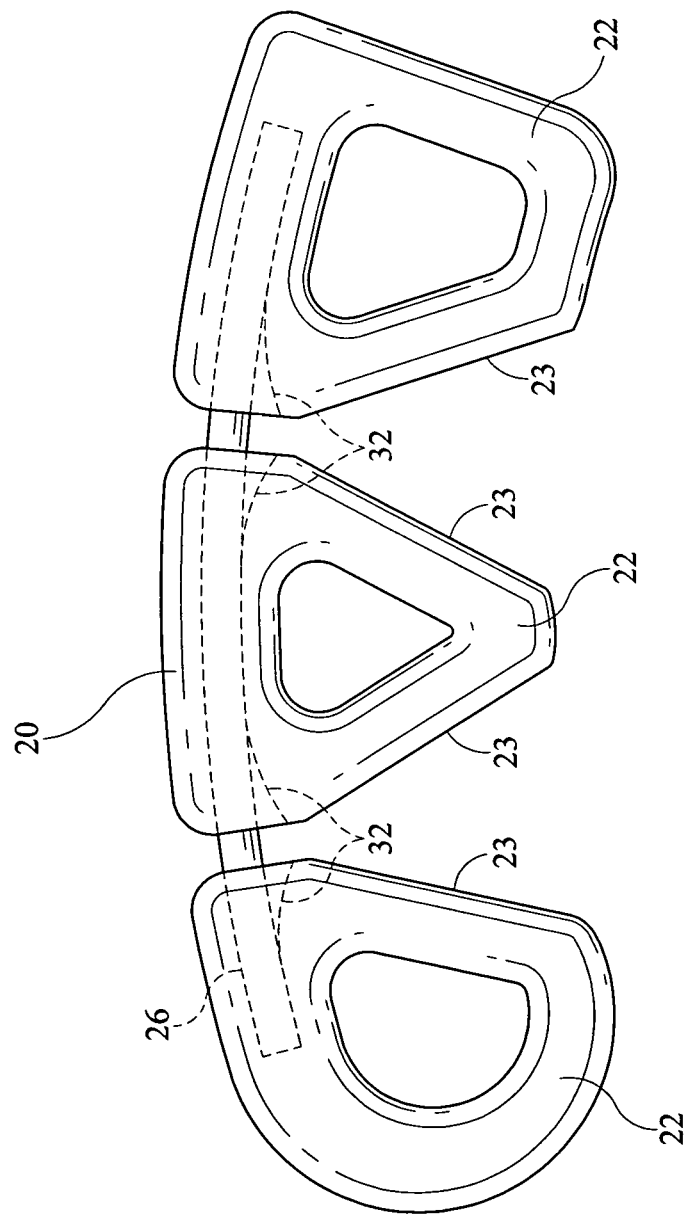
FIG. 16C is a side view, partially in cross-section, of an interbody device showing the placement of a flexible rib therein in accordance with one embodiment of the invention.

FIG. 16C depicts an alternative embodiment of interbody device 20 wherein lobe 22 comprises a plurality of chamfered surfaces 32 at the point where rib 26 enters lobes 22. In the embodiment of FIG. 16C, chamfered surfaces 32 are located below rib 26 such that the rib 26 may flex until it contacts chamfered surfaces 32, or until sides 23 of lobes 22 contact each other. In this embodiment, chamfered surfaces 32 permit maximum flexion of interbody device 20 in one direction, which aids in placement of device 20 into intervertebral space 2.

Figure 16D:
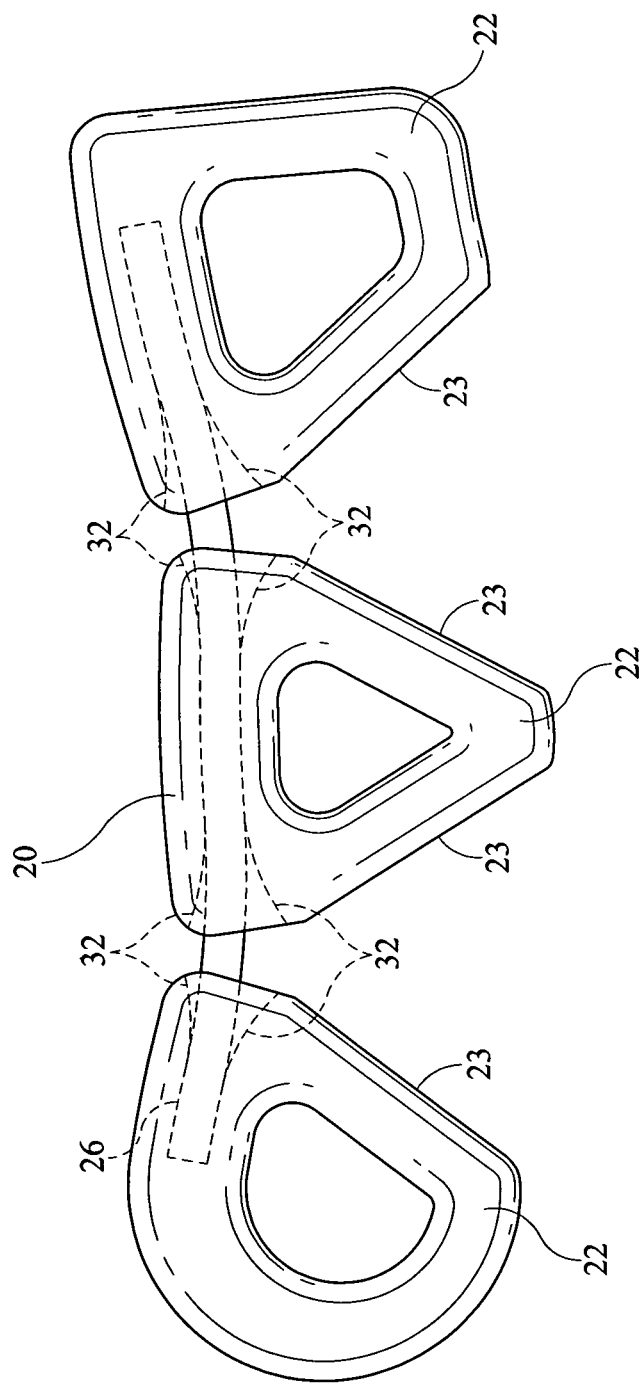
FIG. 16D is a side view, partially in cross-section, of an interbody device showing the placement of a flexible rib therein in accordance with one embodiment of the invention.

FIG. 16D depicts an alternative embodiment of interbody device 20 wherein chamfered surfaces 32 are provided in lobes 22 both above and below the point where rib 26 enters lobes 22, thereby enabling maximum flexion of interbody device in two directions, which assists both in placement of device 20 into intervertebral space 2 and straightening of device 20 for placement into insertion guide 100. In the embodiments of the invention depicted in FIGS. 16C and D, sides 23 of lobes 22 are shaped to contact each other at a point where maximum flexion of interbody device 20 is achieved.

Figure 17A:
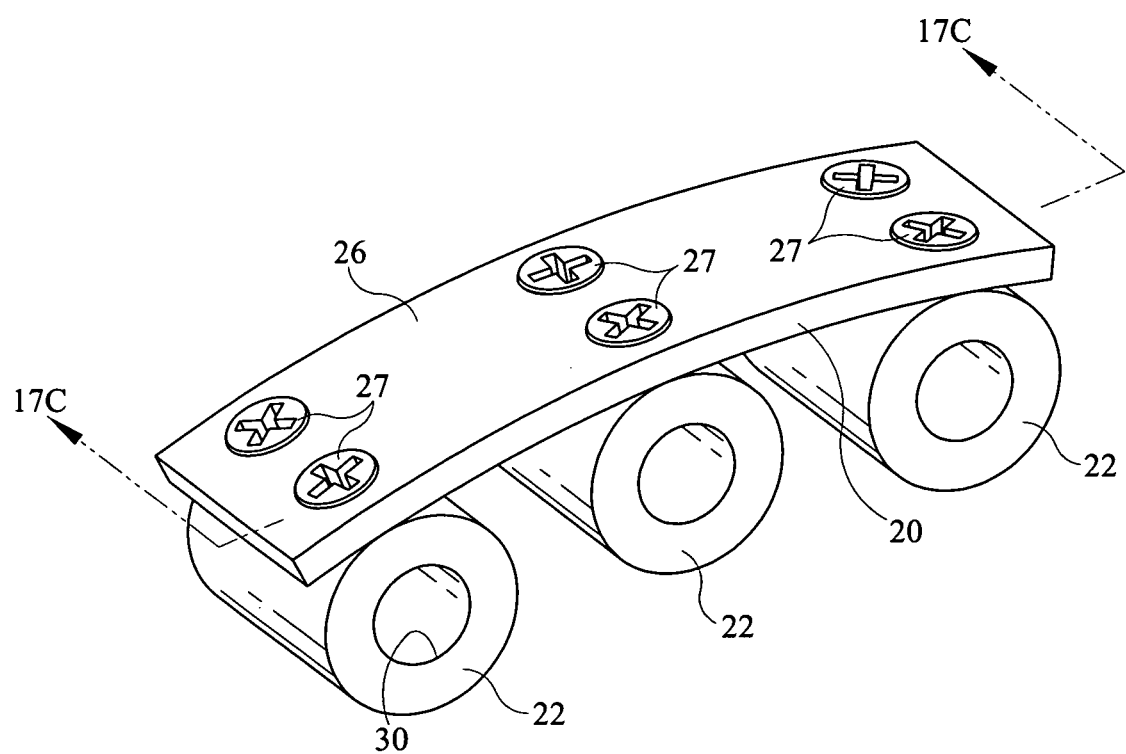
FIG. 17A is a top isometric view of an interbody device in accordance with one embodiment of the invention.
Figure 17B:
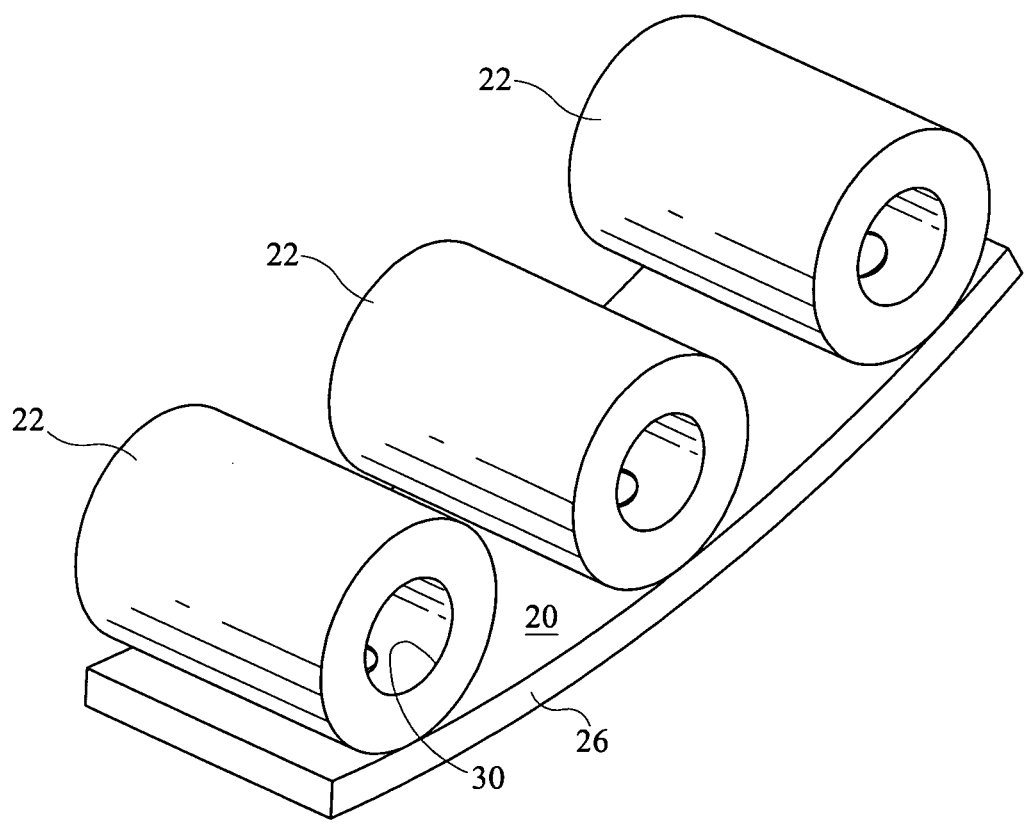
FIG. 17B is a bottom isometric view of an interbody device in accordance with one embodiment of the invention.
Figure 17C:
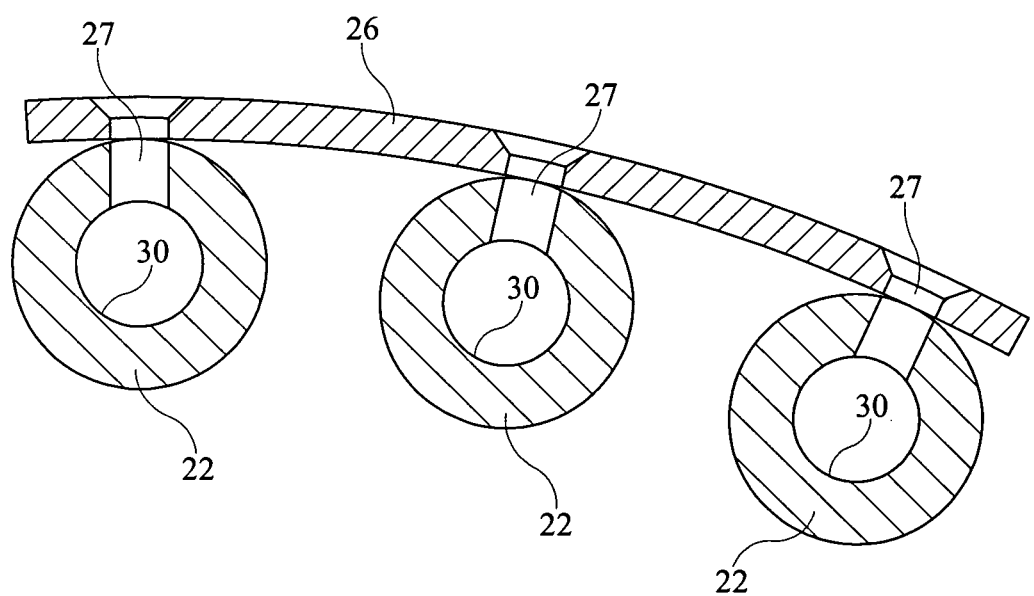
FIG. 17C is a cross-section view of an interbody device taken along the line 17C-17C of FIG. 17A, in accordance with one embodiment of the invention.

FIGS. 17A, 17B and 17C show an alternative embodiment of an interbody device having an exterior central rib 26 preferably comprised of an elastic shape-memory material, for example a memory metal. A plurality of lobes 22 are secured to central rib 26 with a plurality of fasteners 27 that extend through central rib 26 and into lobes 22. In one embodiment of the invention, lobes 22 may comprise tubular elements, as seen in FIGS. 17A-17C, wherein the interiors of tubular lobes 22 may be used for placement of bone graft material to placement into intervertebral space 2.

Referring again to FIGS. 12A-12D, interbody device 20 may further comprise a tab 40 extending from an end of device 20, said tab terminating in a spherical ball 42 for engagement with surface 156 of fingers 152. By providing ball 42, which has a complementary surface for engaging surface 156 of fingers 152, insertion rod 120 may positively engage device 20 until interior rod 140 is advanced outwardly of distal end 122 of insertion rod 120, thereby releasing fingers 152 from engagement with ball 42.

Figure 13:
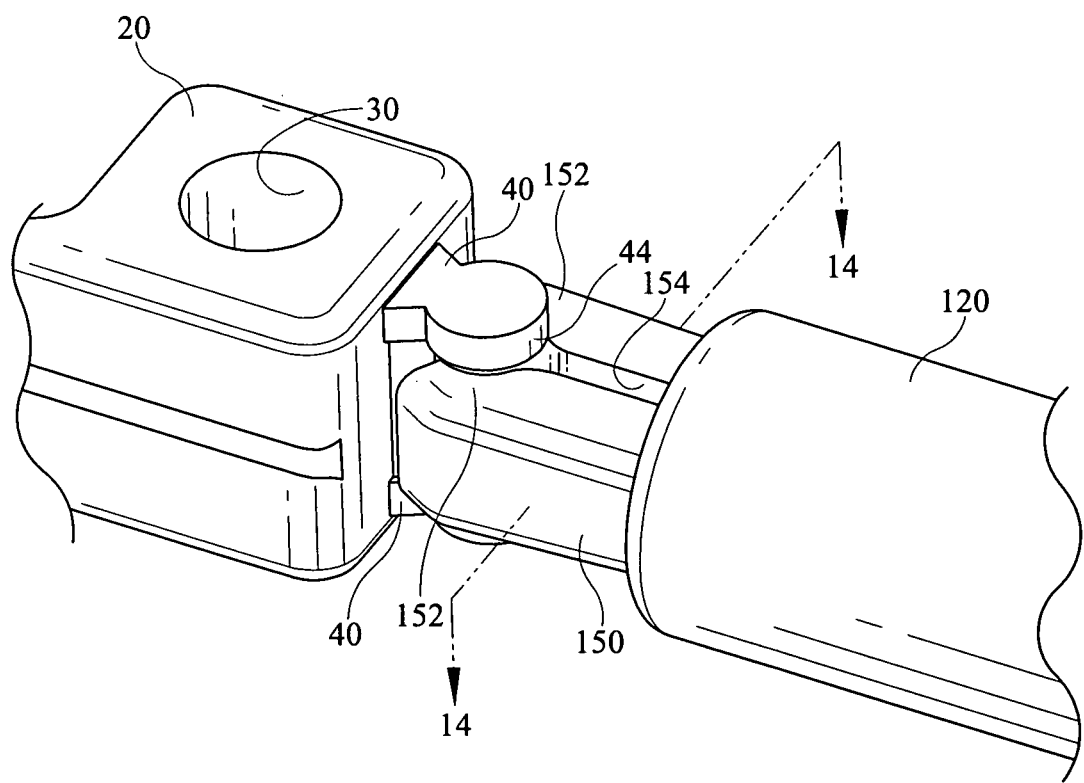
FIG. 13 is a perspective view of an insertion rod secured to an interbody device in accordance with one embodiment of the invention.
Figure 14B:
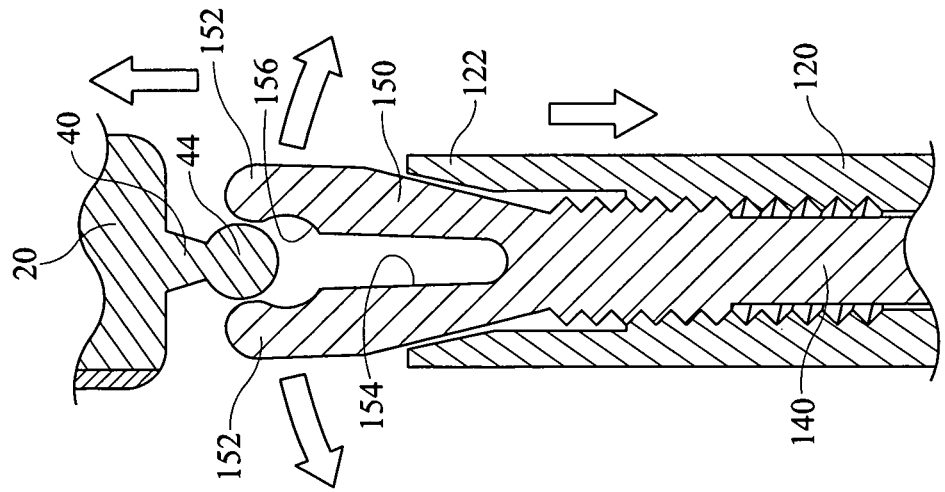
FIG. 14B is a cross-sectional view of an insertion rod releasing an interbody device in accordance with one embodiment of the invention.
Figure 14A:
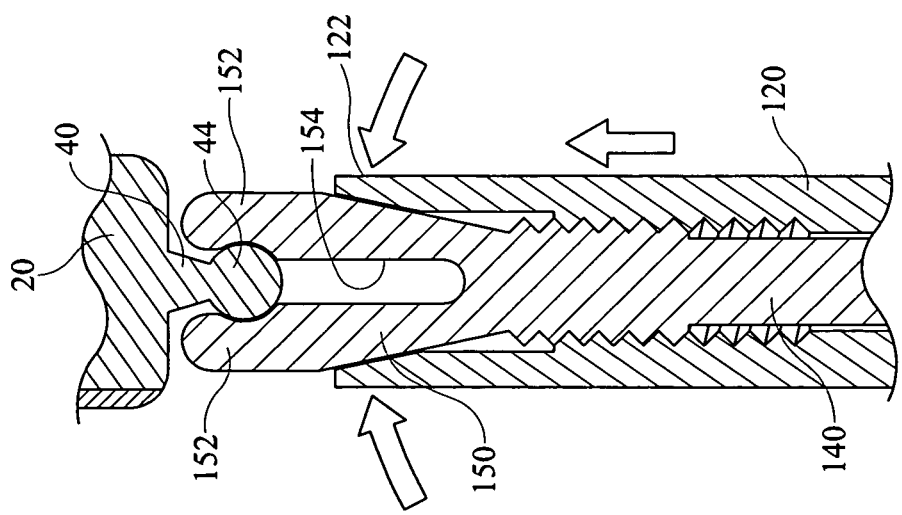
FIG. 14A is a cross-sectional view of an insertion rod secured to an interbody device taken along the line 14-14 of FIG. 13 in accordance with one embodiment of the invention.

In an alternative embodiment of the present invention as depicted in FIGS. 13, 14A and 14B interbody device 20 may comprise a pair of spaced tabs 40 extending from an end thereof, said spaced tabs 40 connected by a cylindrical latch 44 onto which clamp end 150 fingers 152 may grab. Tabs 40 and latch 44 may be comprised of the same material as interbody device 20, for example PEEK, or any other suitable, flexible, bio-compatible material. In this embodiment of the invention, a pair of fingers 152 extends from interior rod 140 for engagement with latch 44. Fingers 152 expand outwardly as insertion rod 120 is rotated and clamp end 150 is advanced outwardly past distal end 122 of insertion rod 120.

Figure 19A:
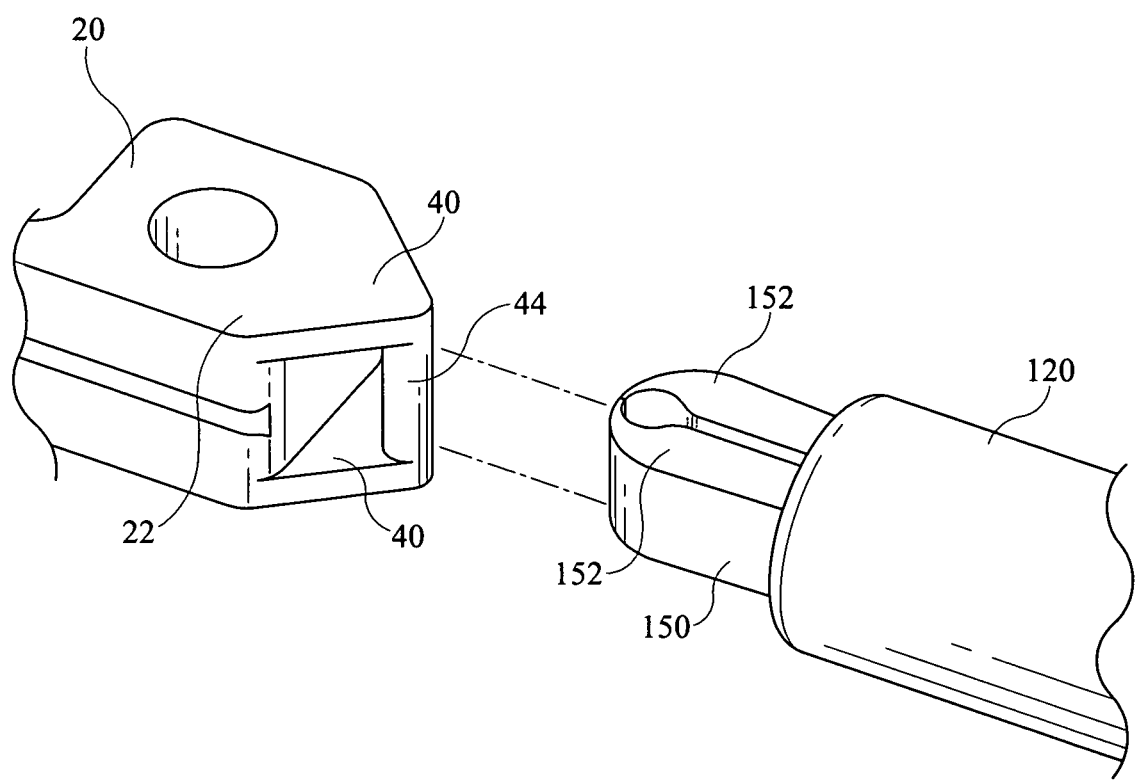
FIG. 19A is an alternative embodiment of an interbody device in accordance with one embodiment of the invention.
Figure 19C:
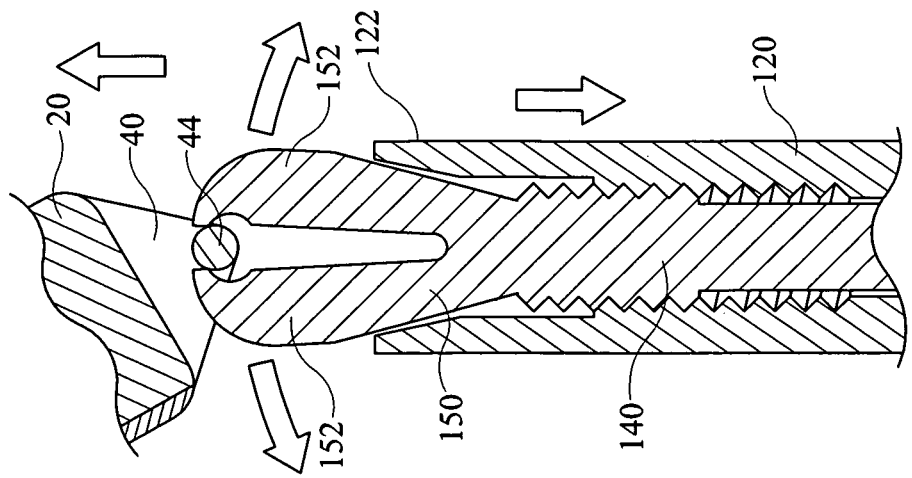
FIG. 19C is a cross-sectional view of an interbody device and an insertion rod in accordance with one embodiment of the invention.
Figure 19B:
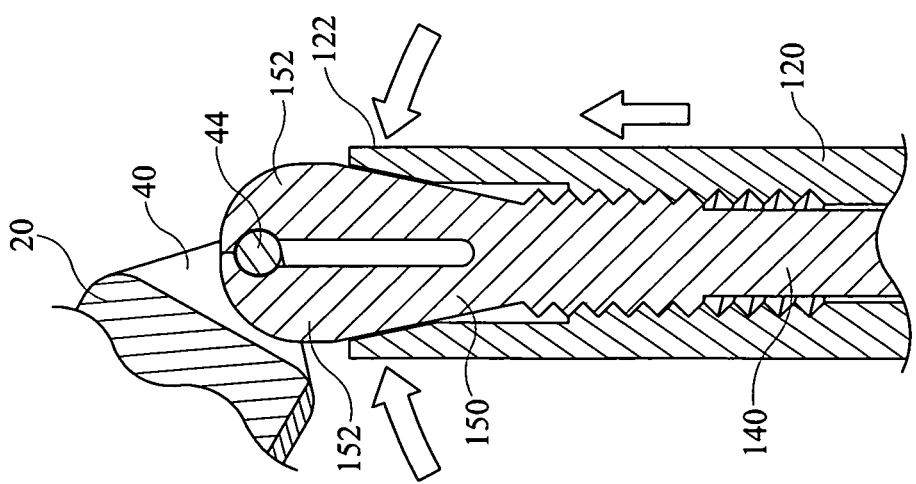
FIG. 19B is a cross-sectional view of an interbody device and an insertion rod in accordance with one embodiment of the invention.

FIGS. 19A, 19B and 19C depict an embodiment of the invention wherein cylindrical latch 44 is separated or spaced from lobe 22 of interbody device 20 by tabs 40, such that fingers 152 are capable of a greater range of rotation around cylindrical latch 44 as depicted in FIG. 19B. This embodiment of the invention permits a much greater degree of curvature of interbody device 20 as it enters intervertebral space 2, since fingers 152 and clamp end 150 of interior rod 140 are capable of rotating nearly 180 degrees around cylindrical latch 44. Detachment of interior rod 140 from interbody device 20 is accomplished by rotation of insertion rod 120, whereby clamp end 150 is advanced outwardly past distal end 122 of insertion rod 120 thus expanding fingers 152 to release latch 44.

Figure 15:
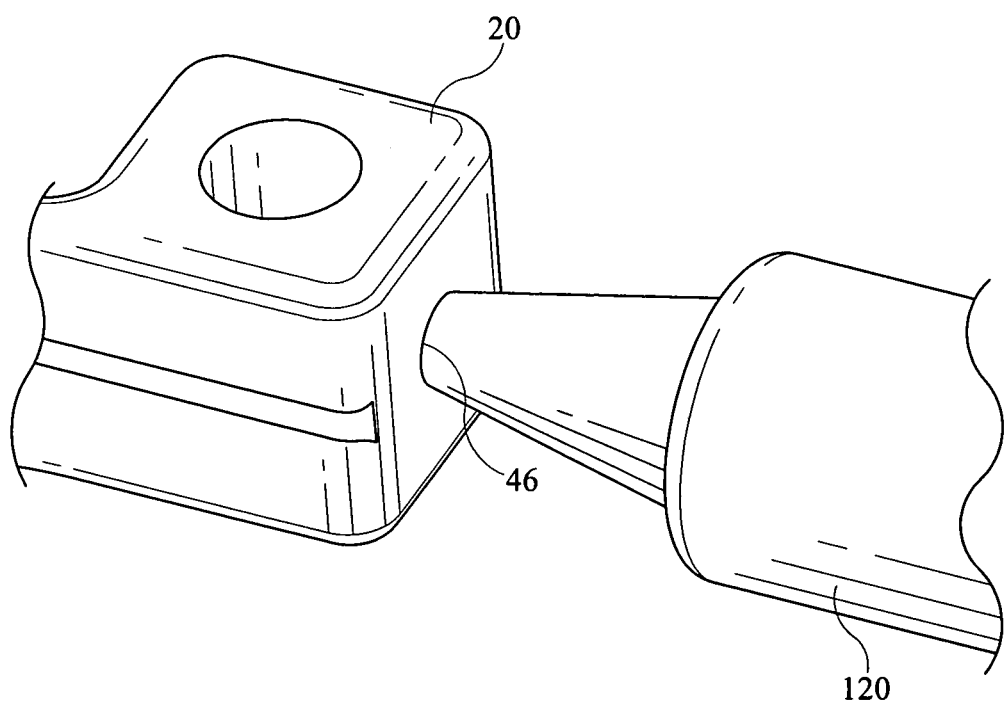
FIG. 15 is a perspective view of an insertion rod secured to an interbody device in accordance with one embodiment of the invention.

FIG. 15 depicts a yet further embodiment of the present invention, wherein insertion rod 120 is formed integral with interbody device 20, and preferably from the same material. Insertion rod 120 is integrally molded with interbody device 20 and connected thereto by a stress riser 46 that is capable of separating rod 120 from device 20 when subjected to a predetermined amount of torque. Once interbody device 20 is properly positioned in intervertebral space 2 insertion rod 120 may simply be rotated such that stress riser 46 eventually breaks, thereby separating rod 120 from device 20. Stress riser 46 may further include a scored portion or stressed portion for ease of separating rod 120 from device 20.

Figure 18A:
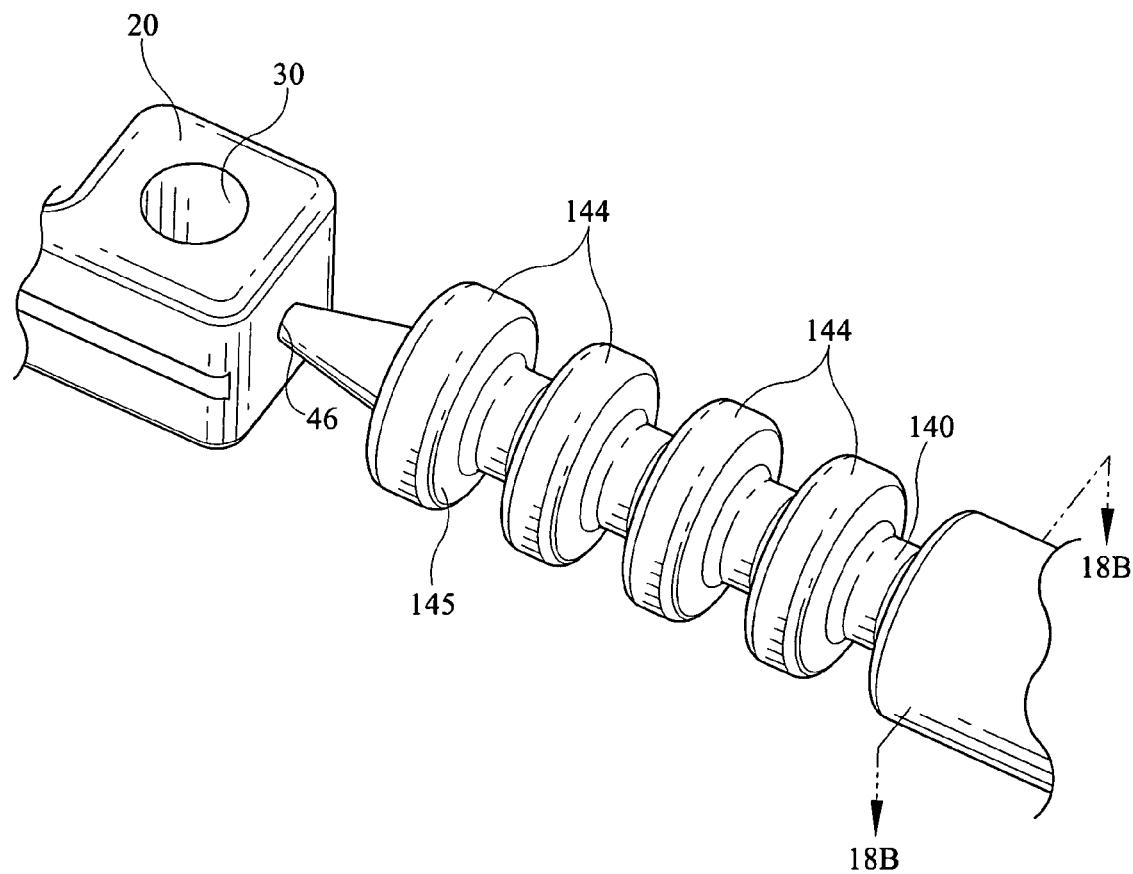
FIG. 18A is a perspective view of an interbody device integral to an insertion rod in accordance with one embodiment of the invention.
Figure 18B:
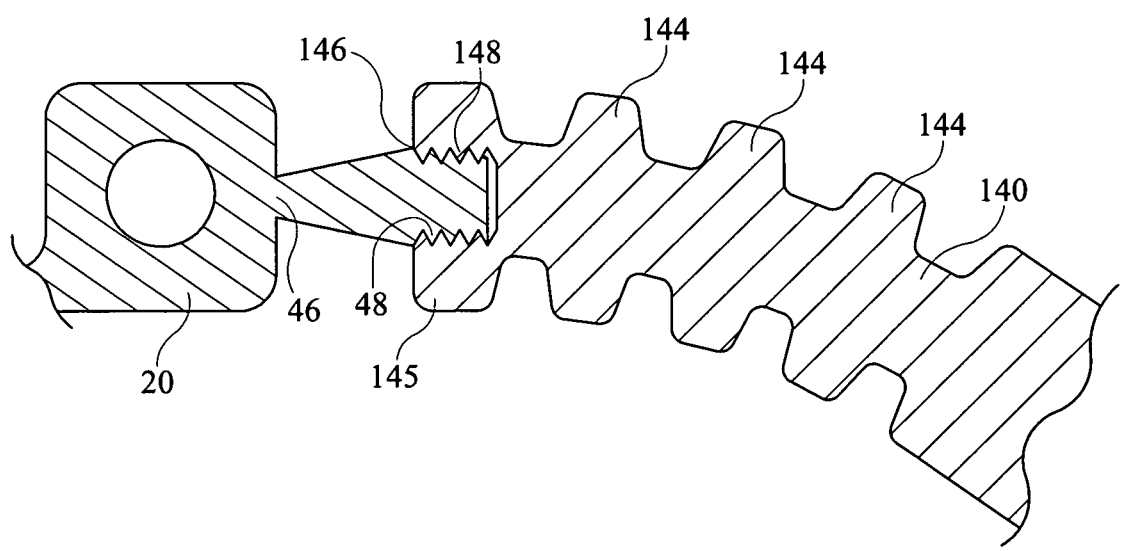
FIG. 18B is a cross-sectional view of an interbody device integral to an insertion rod taken along the line 18B-18B of FIG. 18A in accordance with one embodiment of the invention.

FIGS. 18A and 18B show an alternative embodiment of interior rod 140, wherein interior rod 140 is comprised of a flexible material, for example PEEK or an equivalent flexible, resilient plastic material. Interior rod 140 may comprise a plurality of spaced annular portions 144 that permit flexion of a distal end 145 of interior rod 140. Annular portions 144 are connected by interior rod 140 which has a smaller diameter at distal end 145 to enhance flexibility of distal end 145. As best seen in FIG. 18B, distal end 145 of interior rod 140 may comprise a bore 146 having a plurality of helical threads 148 therein. In this embodiment of the invention, stress riser 46 comprises a plurality of mating threads 48 wherein stress riser 46 may be secured into bore 146 of interior rod 140. Since interior rod 140 is quite flexible, interbody device 20 may be easily positioned in disc space 2, whereupon interior rod 140 is rotated to break stress riser 46, thus separating interbody device 20 from interior rod 140.

Figure 18C:
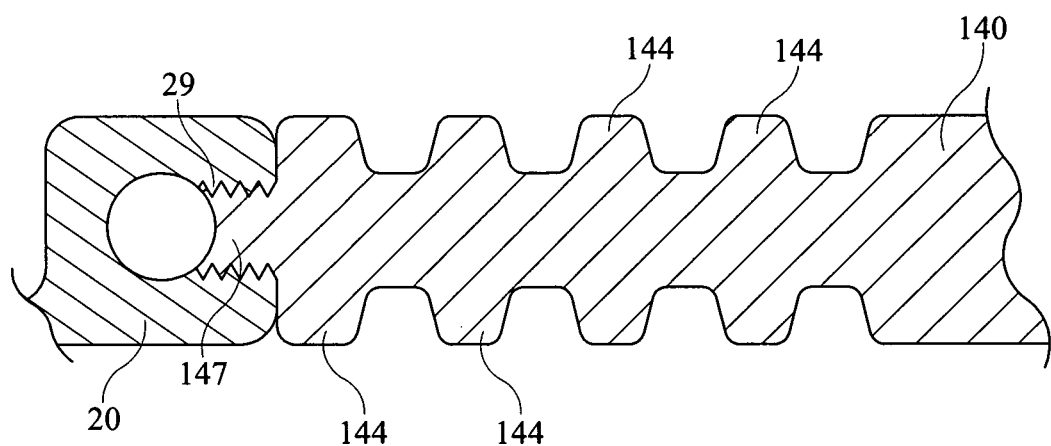
FIG. 18C is a cross-sectional view of an interbody device secured to an insertion rod in accordance with one embodiment of the invention.

FIG. 18C depicts an alternate embodiment of the invention having a flexible interior rod 140 with a plurality of annular portions 144 proximate its distal end 145. Distal end 145 further includes a threaded male end 147 that engages a complementary threaded female end 29 of interbody device 20. In this embodiment of the invention, interbody device 20 is threaded onto interior rod 140 prior to insertion. Once interbody device 20 is placed in disc space 2, interior rod 140 is detached from interbody device 20 by simple rotation. Since annular portions 144 provide the ability to rotate interior rod 140 even when distal end 145 is flexed, detachment of insertion rod 140 from device 20 is easily effected.

Figure 18D:
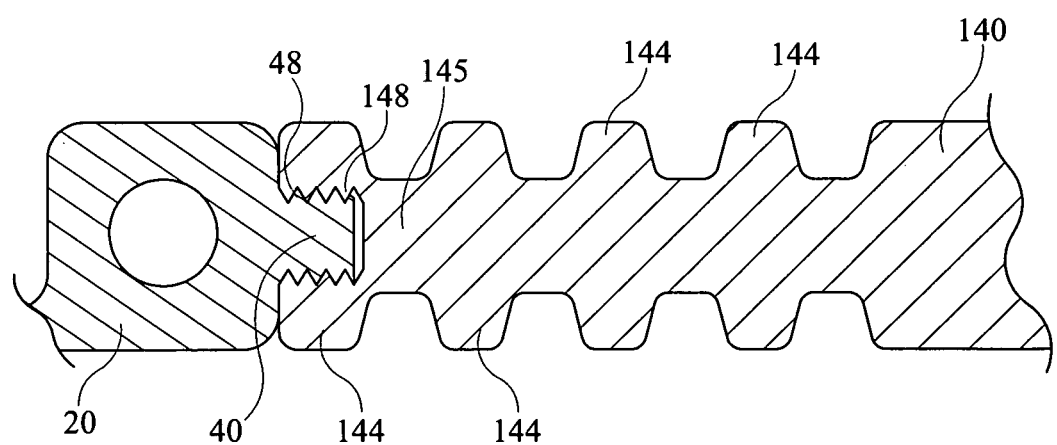
FIG. 18D is a cross-sectional view of an interbody device secured to an insertion rod in accordance with one embodiment of the invention.

FIG. 18D depicts a further alternate embodiment of the invention wherein an interior rod 140 having a bore 146 is engaged by a threaded tab 40. Insertion of interbody device 20 and detachment thereof from interior rod 140 is accomplished by simple rotation of rod 140.

As best seen in FIGS. 1, 10, 11A and 11B, a surgeon may place interbody device 20 in an intervertebral space 2 by first placing insertion guide 100 distal end 104 into intervertebral space 2 through an appropriate incision and positioned for a posterior, postero-lateral, antero-lateral, transforaminal, lateral, far lateral, or anterior approach, depending upon where along the spinal column interbody device 20 is to be used. In FIGS. 1, 10, 11A and 11B, an exemplary posterior surgical approach is depicted, thereby providing a minimally invasive surgical implantation method for interbody device 20. Additionally, as discussed herein above, insertion guide 100 may be secured to a previously located stabilization system 50 to prevent movement thereof, thereby minimizing potential damage to nerve bundles proximate spinal vertebrae 1, and further permitting positive placement and removal of interbody device 20 should the need arise. FIG. 11B depicts the insertion of interbody device 20 delivered through insertion guide 100 having arcuate tip 105 whereby interbody device 20 is positively positioned in intervertebral space 2 as it is forced out of arcuate tip 105.

Figure 10:
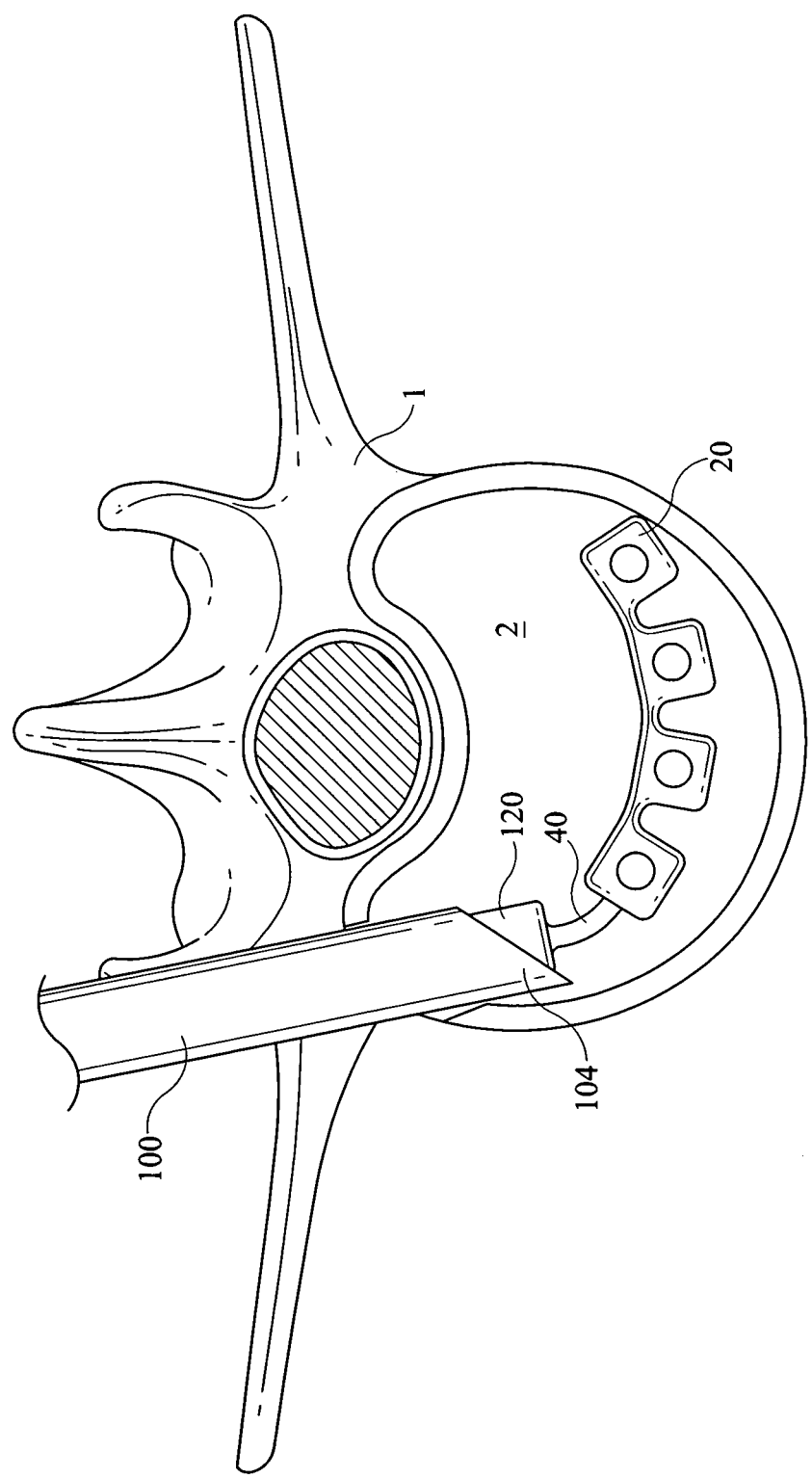
FIG. 10 is a cross-sectional view of an interbody device being inserted into an intervertebral space taken along the line 10-10 of FIG. 1, in accordance with one embodiment of the invention.

Next, interbody device 20 is inserted into proximal end 106 of insertion guide 100. During this insertion, interbody device 20 is necessarily straightened into an "unrelaxed" state. Interbody device 20 is secured to insertion rod 120 by operation of clamp end 150 fingers 152, (unless the embodiment of the invention utilizing an integral interbody device 20 and rod 120 is being employed) and the assembled rod 120 and interbody device 20 are inserted completely into insertion guide 100 in preparation for placement into intervertebral space 2. Once guide 100 is properly positioned, insertion rod 120 is advanced therethrough until interbody device 20 is forced out of a distal end 104 of insertion guide 100 and into intervertebral space 2, as best seen in FIGS. 10 and 11. Once interbody device 20 is properly located in intervertebral space 2 space, it once again retains its relaxed shape due to its shape memory characteristics.

It should be noted that when inserted into intervertebral space 2, guide 100 distal end 104 may be partially compressed due to operation of compression channel 110. This feature of the invention provides a protective channel through which interbody device 20 may pass without concern for damage to adjacent nerves and the like. Interbody device 20 may be shaped such that, when forced through distal end 104 of insertion guide 100, it provides a distraction of guide 100 distal end 104, thereby facilitating its own passage into intervertebral space 2.

At this point in the surgery, the surgeon may take a radiographic image to ensure proper placement of interbody device 20. If dissatisfied, device 20 may simply be removed by withdrawing insertion rod 120 back through insertion guide 100, whereupon adjustments may be made, either to insertion guide 100 placement, or to interbody device 20. Furthermore, the surgeon may employ a trial implant, sized and shaped to approximate the size of interbody device 20 that is ultimately implanted. In this event when a surgeon is not satisfied with the placement of the trial implant it can be removed and exchanged for one of a different size. Additionally, insertion guide 100 may be unlocked from stabilization system 50, moved to present a different entry into intervertebral space 2, then secured in position by operation of collet 62. Once insertion guide 100 is properly positioned, interbody device 20 is inserted into intervertebral space 2, and interior rod 140 is rotated thereby releasing fingers 152 secured to ball 42 or cylindrical latch 44. At this point, rod 120 may be withdrawn back through insertion guide 100, and insertion guide 100 may then be removed.

In a yet further embodiment of the present invention, insertion guide 100 may be shaped or curved to provide for alternative interbody device 20 insertion approaches depending upon the physiological requirements of a specific patient. In this embodiment of the invention, both insertion guide 100 and insertion rod 120 may be made of a flexible material such that the shape thereof may be determined by the surgeon. Alternatively, insertion guide 100 may have a predetermined shape or curvature, while rod 120 is formed of a flexible material, such as a memory metal, for ease of insertion into guide 100.

In this embodiment of the present invention, since interbody device 20 is capable of taking a variety of shapes, it is easily inserted into a curved insertion guide 100, and readily inserted into the disc space by operation of flexible insertion rod 120.

While the present invention has been shown and described herein in what are considered to be the preferred embodiments thereof, illustrating the results and advantages over the prior art obtained through the present invention, the invention is not limited to those specific embodiments. Thus, the forms of the invention shown and described herein are to be taken as illustrative only and other embodiments may be selected without departing from the scope of the present invention, as set forth in the claims appended hereto.

I claim:

1. An interbody device for replacing a disc between adjacent vertebrae or fusing adjacent vertebrae comprising:
a flexible longitudinal rib having a length of shape memory metal disposed therein, said memory metal having a relaxed shape approximating the shape of the disc being replaced, and having a plurality of spaced square-shaped lobes secured thereto and extending from a same side of the longitudinal rib, said lobes each having an upper vertebral contacting surface, a lower vertebral contacting surface, two lateral sides, and an aperture extending from said upper vertebral contacting surface to said lower vertebral contacting surface, said aperture allowing the sides of the lobes to compress or deform slight under load and capable of receiving bone graft material, and wherein adjacent sides from adjacent lobes are connected to each other by a continuous curved surface between said adjacent lobes on an inner portion of said rib to enable flexion of said interbody device, each of the said plurality of lobes having substantially the same size and shape and having a plurality of chamfered edges thereon for contacting said adjacent vertebrae and;
wherein said longitudinal rib and said plurality of lobes have a relaxed shape approximating the shape of the disc being replaced and are capable of being placed in an unrelaxed shape for placement between said adjacent vertebrae.

2. An interbody device as claimed in claim 1 wherein said memory metal comprises a titanium alloy.

3. An interbody device as claimed in claim 1 wherein said memory metal comprises nitinol.

4. An interbody device as claimed in claim 1 wherein said interbody device comprises a polyetheretherketone material.

5. An interbody device as claimed in claim 1 wherein said interbody device comprises a carbon fiber material.

6. An interbody device as claimed in claim 1 wherein said interbody device comprises a memory metal material.

7. An interbody device as claimed in claim 1 comprising:
a tab extending from an end of said interbody device for engagement by an insertion tool.

8. An interbody device as claimed in claim 1 comprising:
a tab extending from an end of said interbody device having an engagement surface thereon for engaging a complementary surface of an insertion tool.

9. An interbody device as claimed in claim 1 comprising:
a bore disposed in an end lobe of said interbody device for releasably engaging an insertion tool.

* * * * *